United States Patent [19]

Carter et al.

[11] E Patent Number: Re. 33,064

[45] Reissued Date of Patent: Sep. 19, 1989

[54] METHOD FOR THE DETERMINATION OF SPECIES IN SOLUTION WITH AN OPTICAL WAVE-GUIDE

[75] Inventors: Timothy J. N. Carter, Minster, United Kingdom; Claus Dähne, Überlingen, Fed. Rep. of Germany; John F. Place, Geneva, Switzerland

[73] Assignee: Prutec Limited, London, Great Britain

[21] Appl. No.: 107,763

[22] PCT Filed: Sep. 8, 1982

[86] PCT No.: PCT/EP82/00195

§ 371 Date: May 18, 1983

§ 102(e) Date: May 18, 1983

[87] PCT Pub. No.: WO83/01112

PCT Pub. Date: Mar. 31, 1983

Related U.S. Patent Documents

Reissue of:

[64] Patent No.: 4,608,344
Issued: Aug. 26, 1986
Appl. No.: 499,164
Filed: Sep. 8, 1982

[30] Foreign Application Priority Data

Sep. 18, 1981 [EP] European Pat. Off. ..... 81810385.5

[51] Int. Cl.[4] ..... G01N 31/06; G01N 33/48

[52] U.S. Cl. ..... 436/34; 356/414; 356/417; 356/418; 422/57; 422/58; 422/68; 435/7; 436/164; 436/805

[58] Field of Search ..... 356/440, 435, 436, 445, 356/448, 414, 417, 418; 422/55-60, 68, 73, 83, 86; 435/7; 436/34, 164, 165, 514, 527, 535, 805

[56] References Cited

U.S. PATENT DOCUMENTS 4,050,895 9/1977 Hardy et al. ..... 250/227

OTHER PUBLICATIONS

Holm et al; Internal-reflection Spectroscopy; Laser Focus, vol. 15, No. 8, Aug. '79 pp. 60-65.

Muller; Spectroscopy with the Evanescent Wave in the Visable Region of the Spectrum; American Chem. Soc. '79, pp. 239-262.

Harrick et al; Multiple Internal Reflection Florescence Spectrometry; Analytical Chem vol. 45, No. 4, Apr. '73, pp. 687-691.

Harrick; Internal Reflection Spectroscopy; Interscience Pub. New York: 1967 pp. 13-65.

"Kinetics of Antibody-Hapten Interaction", Molecular Biology, (1977) pp. 306-338.

"Experimental Methods in Biophysical Chemistry" Ed. Claude Nicolou, J. Wiley and Sons, New York, 1973 pp. 613-647.

Handbook of Biochemistry, Chemical Rubber Company Press, pp. C36-C39.

Gerhard J. Muller, A.C.S. Symposium Series (1979) 239-262.

*Primary Examiner*—Michael S. Marcus
*Attorney, Agent, or Firm*—Herbert Dubno

[57] ABSTRACT

An analyte in solution is made to react with a specific reactant coated on the wave-guide thus modifying the optical properties thereof. The index of refraction of the wave-guide material is higher than that of the reaction medium which ensures that a light signal injected into said guide be carried by multiple total reflection, the distance of penetration of the evanescent wave associated with the totally reflected signal being of the same order of magnitude or greater than the thickness of the analyte-reactant product layer.

16 Claims, 7 Drawing Sheets

| N° | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| $\theta_c$ | 10° | 15° | 20° | 25° | 30° | 35° | 40° | 45° | 50° | 55° | 60° | 65° | 70° | 75° | 80° | 85° |
| $n_{21}$ | 0,174 | 0,259 | 0,342 | 0,423 | 0,500 | 0,574 | 0,643 | 0,707 | 0,766 | 0,819 | 0,866 | 0,906 | 0,940 | 0,966 | 0,985 | 0,996 |

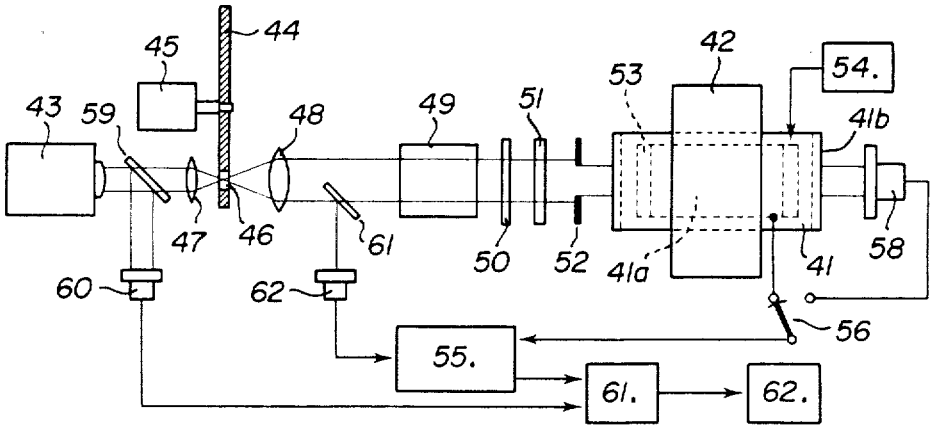
FIG. 13a
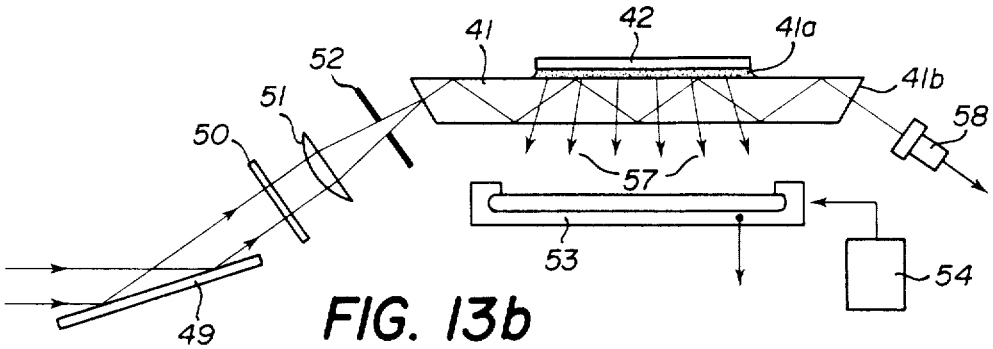
FIG. 13b
FIG. 14
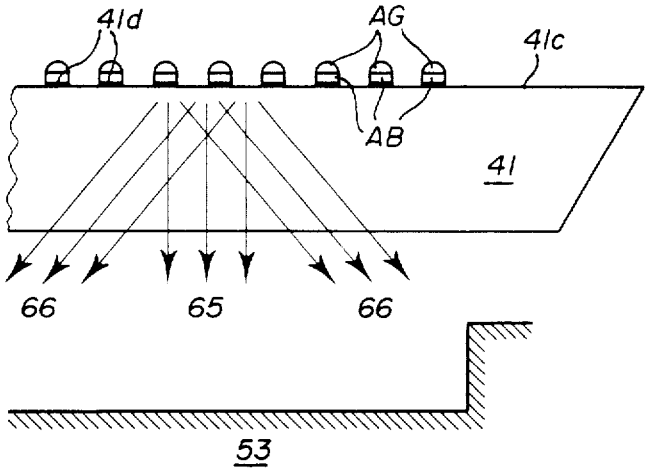

METHOD FOR THE DETERMINATION OF SPECIES IN SOLUTION WITH AN OPTICAL WAVE-GUIDE

Matter enclosed in heavy brackets [ ] appears in the original patent but forms no part of this reissue specification; matter printed in italics indicates the additions made by reissue.

FIELD OF THE INVENTION

The present invention relates to the use of waveguide for the determination of the concentration of a species (or analyte) in solution in a liquid by measuring the rate (concentration dependent) for its combination with or disassociation from a specific reactant thereto, e.g. a conjugate moiety in a complexation reaction. More specifically, the invention concerns a method for determining an analyte in solution in which a layer of analyte-reactant product is formed at the surface of a waveguide into which a light signal is injected and carrying a totally and multiply reflected electromagnetic wave signal and in which the layer changes the optical properties thereof so as to modify said signal, said modification being measured and used for said determination. Thus, the invention applies to a variety of chemical and biological systems and, particularly well, to the determination of bioactive molecules in low concentration by immunoassay type reactions, i.e. reactions based on the formation of complexes by the addition of antibody (AB) to antigen (AG) molecules or vice-versa.

BACKGROUND OF THE INVENTION

Many methods already exist in the field for achieving the above mentioned determination based on the classical techniques of biochemistry. For instance, chemical reactions can be used to detect a given analyte in a number of different ways. Classical systems include titration or reaction with a specific reagent that gives a colored product or precipitate. The requirement for this detection system is that the reagent is in equivalence or in excess, so that the product can be measured by conventional photometry, turbidimetry, colorimetry, etc. The measuring system is chosen according to the magnitude of the signal to be measured. At very low analyte concentrations detection becomes difficult and greater discrimination can be obtained, for example, by concentrating the reaction product locally e.g. by solvent extraction, centrifugation, etc. which may become tedious and costly. However, the above disadvantage was strongly reduced when a practical system for the measurement of biochemical analytes in extremely low concentrations was made available in 1960. This microanalytical system (radioimmunoassay) took advantage of the characteristics of biological systems for molecular recognition (antigen-antibody reactions) and the extreme sensitivity of radioactive measurements (radioactive isotope labelling). An essential feature of this breakthrough was the concept of limited reagent assay with the tracer label used to measure the distribution of the analyte to be measured between the reagent-bound and the free moieties (see for example: Review Paper "The theoretical aspects of saturation analysis" R. P. Ekins in "In vitro procedures with radioisotopes in medicine", International Atomic Energy Agency, June 1970). Although immunoassays were first described as limited reagent assays, equally practical systems were later described for reagent excess methods (see MILES et al. Biochem. J. 108, 611 (1968).

In addition to volumetric and gravimetric analysis, the present methods thus involve highly sensitive methods such as colorimetry, spectroscopy and radio active measurements. However, many of such techniques are now becoming obsolete as they are tedious, require a relatively large quantity of analyte to be accurate, are based on hard to prepare and difficult to store reagents or require expensive and cumbersome equipment and highly skilled operators. Thus, there is a trend now to develop more subtle methods, which require lesser quantities of reagents and which can be performed safely, quickly and accurately by moderately skilled personnel. Among such methods which have been disclosed lately, some involve the use of optical waveguides including the reactant. For analysis, the waveguide is contacted with the analyte in solution whereby a reaction with the reactant on the wave guide occurs with the consequence that the optical properties of the latter are modified. The measurement of such modification then provides the required data for the analyte determination. According to the teaching of some recent references (for instance, U.S. Pat. No. 4,050,895 (HARDY) AND WO No. 81 100 912 (BUCKLES), the guides can consist (BUCKLES) of a porous light transmitting core impregnated with the reactant into which the analyte will diffuse during the reaction. Or, (BUCKLES or HARDY) the waveguide can consist of a non porous light transmitting core (e.g. glass) coated with a porous or permeable sheath impregnated with the reactant and into which the analyte will diffuse. Furthermore, in one specific case applied to immunoassay (HARDY, Example 3), a rod-shaped waveguide is coated with an antibody layer bonded by diphenyldimethoxysilane and reacted with polystyrene latex spheres treated with an antigen. The antigen treated beads will then attach to the guide and modify the light signal output of the latter, which variation is used for the analytical determination.

The above techniques have merit but they can not be readily applied to some typical analyses involving reaction kinetics. Indeed, it is well known that rates may provide essential analytical data, particularly in the case of automated test systems and, since reactions occurring within permeable or porous bodies always involve a preliminary diffusion of the analyte into said body, and since diffusion processes are generally much slower than chemical reactions, the rate of the latter cannot be measured directly; in such a case, only equilibrium data can be obtained. Also in the known prior-art, embodiments are avoided involving the use of a transparent core coated with a reactant sheath with a refraction index smaller than that of the core for the reason that, admittedly, low sensitivity would be expected to result. Indeed in the latter case most of the light signal injected at the input of the guide will travel within the core by a total reflection process and as a result, as is commonly accepted, the interaction of that signal with the reaction products located in the sheath, i.e. outside the core should only be minor. Consequently, care was taken in the prior art that the refractive index of the sheath $n_2$ (where the reaction takes place) be always larger than that ($n_1$) of the core for allowing the light injected in the core at the input to be refracted into the sheath and, from that point on, to continue to travel in the sheath right to the output of the guide. However, contrary to some of the prior disclosures, the output signal (the result of the light having been modified by passing through the products of reaction: reactant+analyte within the sheath) will not readily reenter the core and reach the back end thereof (this behavior results from elementary optical principles to be discussed later), and, for the measurements, the output light detector must be located in the very near vicinity of the testing probe (i.e. the back end of the sheath). Such arrangement is not always practical constructionwise, namely when the guide (plus sheath) is dipped in a liquid for measuring an analyte in solution.

OBJECTS OF THE INVENTION

The present invention remedies these drawbacks as it involves no porous core or sheath and no diffusion through a matrix structure (sheath or core). Also, in the present invention, the light signal travelling inside the waveguide by total reflection is neither transmitted by nor guided within the reactant analyte product; rather, only the evanescent wave component of the signal input (i.e. that part of the wave that extends into the region outside the core in the case of total reflection) is involved. Thus, since the range of action of the evanescent wave is only a fraction of a wavelength ($\lambda$), the quantity of product needed (reactant+analyte) is extremely small and utmost sensitivity with regard to the total amount of species to be analyzed) can be achieved.

Thus, one object of the invention is to provide a method for the fast and accurate determination, with an optical wave-guide, of the concentration of a chemical species or analyte in solution in a liquid. Another object of the invention is to provide an analytical method for determining biological analytes with great specificity and sensitivity. Another object is to provide an analytical method which can be easily implemented by moderately skilled workers and which requires only a minor amount of analytical solution. Still another object of the invention is to provide versatile and automated measuring devices adapted for carrying out the above mentioned method.

SUMMARY OF THE INVENTION

These objects (and still further objects which will appear in the course of this description) are appropriately fulfilled by the present method which comprises using a waveguide core, the index of refraction ($n_1$) of which is selected to be higher than that ($n_2$) of said analyte solution and to provide a ratio $n_1/n_2$ such that the depth of penetration in the solution of the electromagnetic field associated with said light signal travelling in the guide practically matches or exceeds the thickness of the said layer of analyte reactant product. Thus, for instance, the method involves contacting a section of a non-porous light-injected waveguide core coated with a thin film of a reactant specific to an analyte with a solution of said analyte thereby enabling said analyte to react with said reactant of the film and form a reactant-analyte product layer, observing the corresponding optical changes with time occurring to the light signal travelling through the core at the output of said core as the result of said product layer formation and comparing the rate data obtained with standard reference data obtained in s similar manner from calibrating samples of said analyte, the refractive index ($n_1$) of said core being greater than that ($n_2$) of said solution and the thickness of said film being only a fraction of the signal wavelength.

BRIEF DESCRIPTION OF THE DRAWING

These and other objects and features of the present invention as well as advantages thereof will become more readily apparent from the following description of certain preferred embodiments thereof made with reference to the accompanying drawings in which:

FIG. 10 represents schematically on an exaggerated scale, a fiber optic probe usable in the apparatus of FIG. 9;

FIG. 10b is a side sectional view thereof along the line B—B of FIG. 10a.

FIG. 11 is a schematic representation, on an enlarged scale, of another probe embodiment particularly adapted for light mode variations measurements.

FIG. 12 is a diagrammatic representation of the light signals at the detector of an apparatus similar to that in FIG. 9 but used for fluorescence measurements.

FIG. 13a represents schematically (top view) an apparatus for measuring optical changes caused in a wave guide by light scattering.

FIG. 13b is a partial schematic side of the apparatus of FIG. 13a.

FIG. 14 represents schematically on an exaggerated scale part of a modification of the embodiment of FIGS. 13a and 13b.

FIG. 18b is a cross-sectional view of a portion of such apparatus along line A—A in FIG. 12a.

DETAILED DESCRIPTION OF THE DRAWINGS

Physical insight into the interaction mechanisms at a reflecting surface can be obtained from a more fundamental approach with the aid of Maxwell's equations. In the present case, i.e. reflection in a dense medium at the boundary with a rare medium, the following question must be answered: what is the electromagnetic field distribution in the rarer medium beyond the reflecting interface for total internal reflection?

Figure 1:
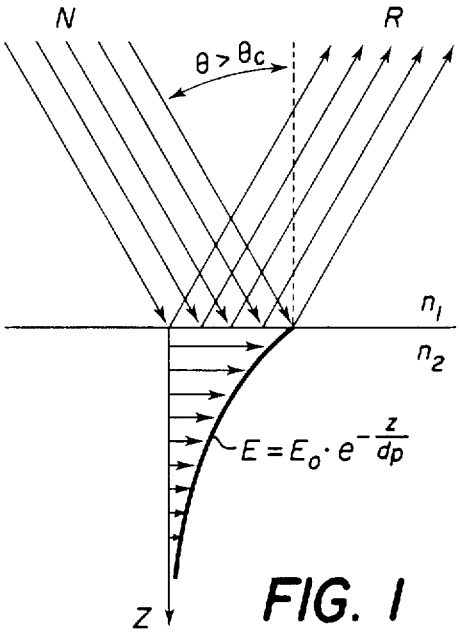
FIG. 1 illustrates schematically the total reflection process of an incident beam N at the boundary between a dense ($n_1$) and a range ($n_2$) medium at an $\theta$ larger than $\theta_c$, the critical total reflection angle. In this figure, $E_o$ is the initial magnitude of the electric field component of the light at zero depth in the rarer medium, Z is the depth of penetration axis and $d_p$ is defined in the discussion below. R is the reflected beam.

In this case, there exists a wave function in the rarer medium which propagates parallel to the interface. Its electric field amplitude falls off exponentially with distance from the surface (see FIG. 1); therefore it is called an evanescent wave. In the ideal case and if the rarer medium has no absorptive property of its own at the wavelength considered, there is no net flow of energy into the nonabsorbing rarer medium, since the time average of the energy described by Poynting's vector (see, for instance M. BORN & E. WOLF, "Principles of Optics" Pergamon Press (1959)) is zero. Mathematically, the electric field can be described by the exponential function:

$$E = E_0 \cdot e^{-\frac{Z}{cp}}$$

Figure 2:
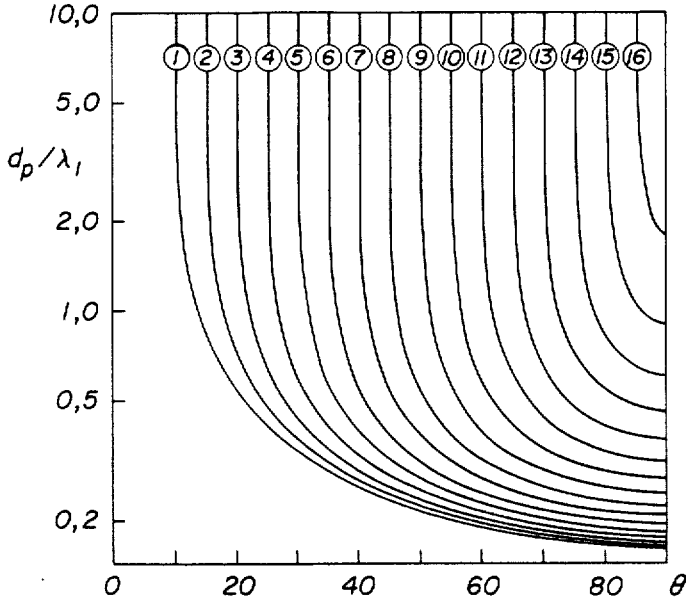
FIG. 2 illustrates the fractional penetration depth of electromagnetic field in rarer bulk medium for total internal reflection versus angle of incidence for a number of interfaces. The penetration depth is infinitely large at the critical angle and is about one tenth the wavelength at grazing incidence for relatively high index media. $\lambda_1=\lambda_1$ is the wavelength in the denser medium. (Taken from N. Y. HARRICK, Internal Reflection Spectroscopy, Wiley 1967).

The depth of penetration $d_p$, defined as the distance required for the electric field amplitude to fall to $e^{-1}$ of its value at the surface, is given by $$d_p = \frac{\lambda_1}{2\pi(\sin^2\theta - n_{2-1}^2)^{\frac{1}{2}}}$$

where $\lambda_1 = \lambda/n_1$ is the wavelength in the denser medium and $n_{2\text{-}1} = n_2/n_1$ is the ratio of the refractive index of the rarer medium divided by that of the denser medium. The meaning of these relations is illustrated by FIG. 2 in which the penetration depth divided by the incident and reflected wavelength $\lambda_1$ is plotted versus the angle of incidence $\theta$ for a number of interfaces (i.e. for different ratios of $n_2/n_1$). It should be noted that the penetration depth is only about one-tenth the wavelength in the cases when the difference between the refraction indices is large, i.e. when $n_2/n_1$ is small, this being near the grazing angle ($\theta = 90°$). This penetration becomes indefinitely large as $\theta$ approaches $\theta_c$. At a fixed angle, the penetration depth is larger in the case of small index differences (i.e., as $n_{2\text{-}1}$ approaches 1). The penetration depth is also proportional to wavelength and hence is greater at longer wavelengths. As an example the dense medium can be glass ($n_1 \approx 1.5$) and the rare medium an aqueous analyte ($n_2 \approx 1.3$); $n_2/n_1 = 0.867$ which corresponds approximately to curve 11 of FIG. 2. In this case, the penetration would be about ⅓ the wavelength at the grazing angle, theoretically infinite at the critical angle (60°) but already below 1 at 65°.

Figure 3:
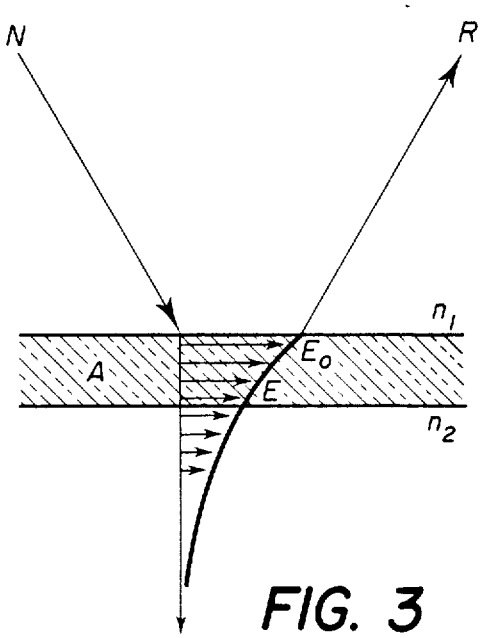
FIG. 3 illustrates the interaction of an evanescent wave and a layer of reaction product.

Since E decreases exponentially, the region beyond the boundary interface in which the amount of energy for interacting with the product is still significant corresponds to the depth Z where the electric field magnitude is still a reasonable fraction of $E_o$, say a value of at least 0.1 $E_o$, better, the region in which E is between $E_o$ and $E_o/3$. Thus, for optimum interaction efficiency, the thickness of the reaction product film should approximately match the depth of that region. This is illustrated on FIG. 3 which shows an incident (N) and a reflected beam (R), the zero depth vector $E_o$ of the evanescent wave and a film of product reactant plus analyte (A), the thickness of which approximately matches the penetration depth $d_p$ where E is about $E_o/3$. In FIG. 3, the influence of the refractive index of the thin film A is not considered significant because the thickness of this film does not exceed the depth of penetration of the evanescent wave. Indeed, the change of refraction index of the rare medium due to the growing of the analyte-reactant film in the reaction area is so small that the corresponding change of the value of the critical angle of reflection is practically negligible except for the reflecting modes quite close to that reflecting angle. Support to this view which constitutes an unexpected advantage of the invention over the prior art can be found for instance in the aforesaid N.Y. HARRICK reference, p. 51.

Another point which should be emphasized for comparison with the prior art concerns the efficiency of the interaction of the light signal with the reaction product. In the classical spectrometric systems, a light signal is passed through a transparent holder containing the analyte (beaker or cuvette) and part of the energy is absorbed by the sample which leads to some degree of absorption that is measured. Yet, this method is not particularly efficient as the amount of analyte should be relatively large to provide significant interaction with the light signal under usual conditions. In contrast, in the present invention where the interaction of an evanescent wave with a film the thickness of which approximately matches with the penetration of that wave is involved, the efficiency is considerably higher since there is a strong light amplification effect in the interaction area. Indeed, as shown for instance in the previously mentioned HARRICK reference, the field strength of the evanescent wave within its range of interaction with the analyte-reactant layer is much stronger than that of the incoming signal. This is actually due to the simultaneous presence of both the incoming and outgoing beam field amplitudes.

The above discussed optical fundamentals useful for understanding the operating principles of the invention refer to the use of unpolarized light. In practice, it is important to note that the initial magnitude of the electric field at zero depth ($E_o$) is dependent on the state of polarization of the incident light wave. Thus, in some cases, polarized light in place of ordinary light can be advantageously used in practising the invention (it will be seen hereinafter that in case of measuring signal changes by ellipsometry, polarized light is essential) and, in some cases, the various optical parameters can be controlled and optimized for maximum response and sensitivity; for instance a selection of an appropriate incident polarization angle (e.g. polarization parallel or perpendicular to the plane of incidence) can be made for maximizing $E_o$.

In view of the above considerations, the following advantages of the invention relative to the prior art can be fully appreciated. Thus, in the case of a test involving one particular specific reactant for an analyte, the thickness of the product layer will usually be determined by the respective size of the product molecules. For instance, in a typical immunoassay, the product layer may be constituted of a first film of an antibody and a second film of an antigen. The thickness of this may range depending on the molecule types from several Angströms to several hundreds of Angströms or more. Now, in view of the thickness of the layer, the index of refraction of the core may be selected and also in some cases the wavelength so that the above discussed parameters will be matched as much as possible. To give an example by way of illustration, if the layer involved is relatively thin, cores with high refractive indices will be selected (for instance, sapphire, $n=1.8$; silicon, $n=3.4$) and, if compatible with the optical processes involved (i.e. absorption), scattering, fluorescence, etc.), shorter wavelengths will also be selected. This will permit minimizing interaction of the evanescent wave with regions of the analyte solution deeper than the thickness of the space where the analytical reaction is taking place, thus minimizing the influence of undesirable extraneous factors (background noise, presence of impurities in the solution and the like). Obviously, none of the methods of the prior art can achieve such possibilities. It should also be kept in mind in appreciating the differences between the present invention and the prior art where the thickness of the sheath extends well beyond the penetration of the evanescent wave (whereby the refractive index ($n_2$) of the sheath becomes determinant in contrast with what happens in the invention) and in which $n_2$ is made greater than the index ($n_1$) of the core, that the light signal initially injected in the core and refracted into the sheath will not readily reenter into the core and be present at the output thereof as apparently believed by some (see for instance WO No. 81 100 912). Indeed, when a light signal is travelling in a rarer medium surrounded by a denser medium, refraction of said light signal into the sheath will occur. Then, this refracted wave will be totally reflected by the outside boundary of the sheath and will bounce back toward the core. Now, since the index $n_1$ of that core is smaller than that of the sheath, the wave will do either of the two following things: if the incident angle is larger than the critical angle, the wave will be again reflected and will stay definitely in the sheath. If the incident angle is smaller than the critical angle, the wave will go through the core and penetrate on the other side into the sheath and so on. So, in no case will a wave originally injected into the core and having been refracted in the sheath return solely in the core and be present therein at the output of the core unless it is still surrounded by the sheath. This is perfectly illustrated in FIG. 3B of U.S. Pat. No. 4,050,895. No shortcoming of that sort exists with the invention in which the key light signal only travels within the core and not in the outside layer containing the reactant and analyte.

The optical changes involved in the method of the invention can relate to different kinds of phenomena; for instance, the following phenomena can be involved: absorption of the light travelling in the core; scattering of the light signal by the reaction product; fluorescence of the reaction product upon excitation by the light signal in the core. Further, the excitation signal in the core can be polarized and ellipticity polarization factors may be subject to modification by the analytical reaction and be monitored. Each of the these possibilities are disclosed in more detail hereafter in this specification.

The types of analytical measurements which can be accomplished with the present method are so many that it is practically impossible to list them all. However, a few examples will be given hereinafter by way of illustration. However, before going any further in this direction, it is useful to develop somewhat the fundamentals pertaining to the application of the invention to "limited reagent" and "excess reagent" assays desirably used in biological and diagnostic analysis. For the purpose of such discussion, we shall conventionally call the analyte the "antigen" AG and the reagent the "antibody" AB. Needless to say that the reverse condition is also valid.

"Excess reagent" assay refers to cases in which an excess of a reactant in respect to the analyte is used. "Limited reagent" essentially involves the use of a system in which the test substance or analyte (containing) the antigen to be measured) is treated with a limited amount of a specific reagent (the antibody) to give an analyte-reactant product (e.g. an AG.AB complex) plus some residual analyte. When the reaction is allowed to go to completion, i.e. if the assay proceeds to equilibrium ("saturation assay"), that is, the limiting conjugate reagent (AB) is saturated with the analyte, it is necessary to add, prior to the reaction (or, in sequential assays, at some time before the final equilibrium is reached, i.e. prior to measurement), a fixed amount of a labelled form of the analyte (AG*) to the reaction mixture being under test. For the example of an antigen to be assayed with an antibody reagent, the proportion of the labelled antigen (AG*) to the unlabelled one (unknown) shall stay the same in said residual analyte as it was at the start. Since the known amount of AB used will bind a known amount of the AG+AG* mixture, it suffices to determine the residual AG* or the AG* bound to the AB (by means of its label) to calculate the amount of AG originally present in the sample. To give a simplified example, suppose that the sample contains x equivalents of an enzyme (AG) to be measured by means of a known amount g of an enzyme conjugate (AB) that forms an AG.AB complex (with, for instance, a 1:1 molecular ratio of both components). Then, prior to the reaction, a equivalents of the same enzyme to be measured but in labelled form (AG*) are added to the sample. Thus, in the course of the reaction, a poprtion of g equivalents of antigen (AG+AG*) is consumed by the g equivalents of antibody. Now after removing the complex from the mixture, the residual AG* is ascertained by conventional means. If it is found, by subtracting the value measured for the remaining AG*, that the amount actually used up was b equivalents, it becomes evident, since AG and AG* are chemically identical and consumed at the same rate, that the ratio of consumed AG* to consumed AG, i.e. $b/g-b$ should be equal to the original ratio $a/x$, from which $x=a(g-b)/b$ can be calculated.

This type of approach is quite attractive although, in the prior art applications, it suffers from some drawbacks, one of them being the general requirement that the complex (mixture of AG*.AB+AG.AB) must be separated from the reaction medium which is sometimes tedious and a possible source of errors. Now, when applied to the present invention, this drawback is nonexistent because the complex that forms automatically removes the analyte from the solution as it deposits onto the waveguide. To illustrate the application of the present method to "saturation type assays" one shall again begin with a waveguide, say an optical fiber coated with a specific antibody AB which is immersed into a buffer solution and allowed to equilibrate with it. The unknown amount of complementary antigen AG to be determined is then added as before but simultaneously with a known small amount of the same antigen labelled with a molecule having specific optical properties (AG*) e.g. optical absorption, fluorescence, etc.) which may be detected by the evanescent wave interaction at the surface of the coated fiber using suitable optical arrangements to be described in this specification. Now, since both labelled and unlabelled AG are essentially identical in reactivity species can be detected via its label, the apparent change in the optical property detected through the fibre (e.g. fall in absorbance if an absorbing label is used) will be inversely proportional to the unknown concentration of AG and can be determined with reference to a suitable series of known standards. This kind of application is illustrated in one of the Examples hereinafter.

At this point it is useful to make a clear statement concerning the label used to measure the reaction that takes place. Normally, in immunoassays, it is not possible to measure the analyte directly because the concentrations of analytes and reagents are extremely low. Since the equilibrium mixture in limited reagent assays essentially only contains excess analyte and a fixed amount of bound complex, when the former cannot be measured directly and the latter is a fixed amount, no quantitative estimation of the original analyte concentration can be obtained even after separation of the complex and the excess antigen. The added labelled tracer (a small quantity of labelled analyte) is necessary to allow measurement via the label according to its distribution between the bound moiety and the free moiety.

If the analyte, however, has an intrinsic property that can be detected when it is concentrated locally (i.e. in situ separation and in situ concentration), e.g. on the surface of a fiber optic probe, then the addition of a labelled analyte tracer is no longer necessary. Thus, in the present invention, the in situ concentration of the analyte-reagent complex may allow for the detection of the analyte without resort to a labelled tracer. However, local concentration of the analyte reagent complex (since the amount of reagent is fixed) will not allow the quantitative determination of the original analyte concentration unless the reaction between analyte and reagent is measured kinetically or unless the total amount of analyte is less than the number of reagent bonding sites. Thus, being the in situ separation and concentration of the complex bound analyte in conjunction with a sensitive detection system in the kinetic mode as in the present invention allows quantitative detection of the analyte in limited reagent system without resort to a labelled tracer.

As far as labelled systems are concerned, a distinction can be drawn between tracer systems in which a labelled version of the analyte is added in trace amounts to the reaction and the labelled reagent systems in which a label is attached to the specific reagent.

The former tracer reagent is normally used in limited reagent assays (e.g. standard radio immunoassays), while the latter is normally used in excess reagent assays (e.g. standard sandwich assays) and can be used in certain forms of kinetic reagent assays (e.g. KRONICK et al, U.S. Pat. No. 3,939,350); labelled analyte and labelled reagent systems are suitable for the present invention if the label used is capable of being detected in an optical waveguide system (e.g. absorbing or fluorescent labels).

Figure 8:
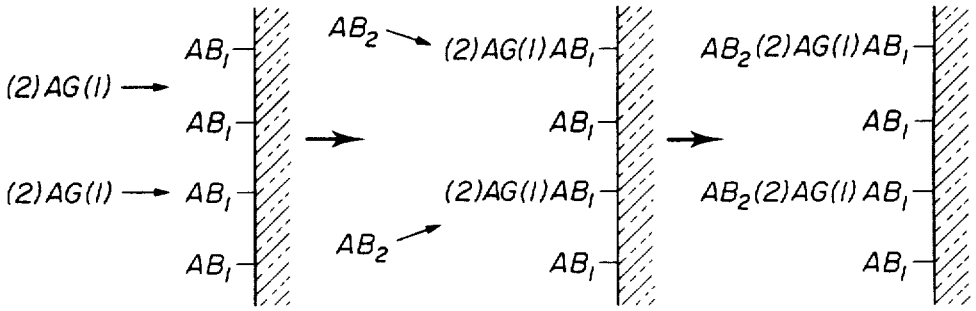
FIG. 8 is a diagram illustrating a "sandwhich" type assay.

FIG. 8 is a diagram illustrating a "sandwich" type assay.

Figure 4:
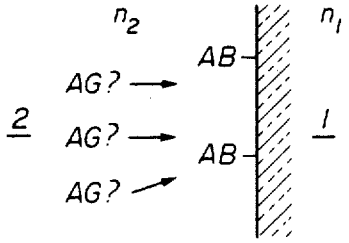
FIG. 4 is a diagram illustrating a first type of assay called "direct type of assay".
Figure 5:
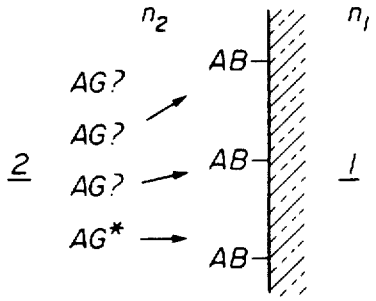
FIG. 5 is a diagram illustrating a competitive "limited reagent" type of assay.

The most straightforward case of assay to which the invention is applicable is schematized on FIG. 4. This is called the "direct" type assay. In this assay, a waveguide core 1 of which only a portion (with refractive index $n_1$) is represented is provided with a film of antibody AB and this core is immersed in an analyte solution having refractive index $n_2$ ($n_1 > n_2$) containing an antigen AG? to be determined. The antigen will attach to the AB molecules at a rate proportional to the antigen concentration [AG?] (since the amount of AB film on the core is a fixed entity) and when this rate is determined, it can be correlated with standard rates obtained from calibrating AG solutions and [AG?] can be determined. So, the amount of AB available can be "limited" or it can be in excess and the reaction can go to an equilibrium. For detecting the AB-AG complex formation by means of the optical changes occurring in the core, the various aforesaid techniques can be used (i.e. extinction of the signal by absorption, scattering and fluorescence phenomena, etc.), provided the formation of AB.AG generates the required optical changes. So, the test applies particularly well to large molecules able to scatter light or having observable properties at determined wavelengths. If such properties are missing, then the test is of little value and a "limited reagent" competitive type test shell be preferable used with an amount of labelled AG (AG*) added to the analyte. This is illustrated in FIG. 5 in which the signs (letters and numerals) used are like those in FIG. 4. In this test, the amount of AG* needs not to be known provided it is standardized (i.e. always constant for a set of calibration curves and tests), since the rates of the analytical reactions with various quantities of AG? will always be in direct relation to the AG*/AG? ratio (being naturally kept in mind that the observable optical change in the wave guide is due only to the labelled reaction product AG*-.AB).

Figure 6:
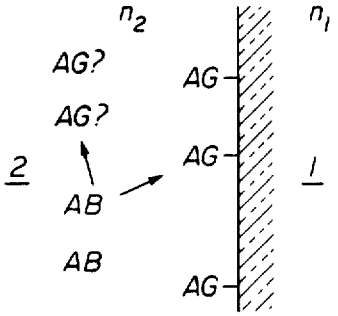
FIG. 6 is a diagram illustrating an indirect competitive "limited reagent" type assay.
Figure 7:
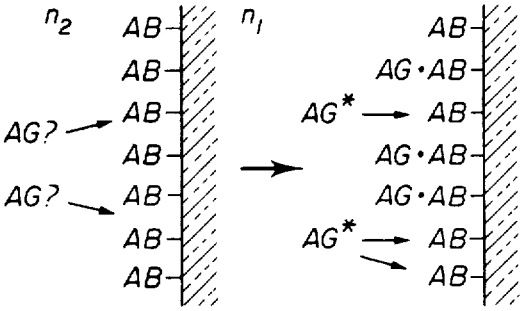
FIG. 7 is a diagram illustrating a sequential "saturation" type assay.

In another very useful variation of the "limited reagent" type assay, the wave-guide core is coated with a known or fixed amount of the same antigen (preferably in pure form) which should be determined in the analytical sample, after which the core is contacted with the sample and, simultaneously, a fixed amount of free detectable antibody is added. This is illustrated in FIG. 6 in which the signs are the same as used before. It is seen from this figure that the reference amount of antibody AB will simultaneously react with the reference AG on the core and with the AG? to be measured. Thus, the observed rate (as depicted by the optical changes occurring in the core) will be related to the AB/AG? mole ratio and correlation with standard reference rate curves will provide the desired results. Obviously, in this case the AB must have observable properties in the optical method used for the test, i.e. AB can have absorbance at suitable λ's or be adapted to scatter light or the like. Alternatively if AB is not directly observable on the guide when reacting with AG, it can be labelled e.g. coupled with a fluorescent or any other optically detectable label.

Still another system involves the so-called sequential testing core is contacted with labelled AG* which will fill the voids in the antibody layer on the core. Measuring thereafter or during reaction the optical changes due to the label of AG* will give the necessary data for calculating the original amount of AG?.

Finally, the present invention also applies well to the assay case called "sandwich" assay relating to the determination of antigens having more than one bonding sites for antibodies, i.e. antigens having sites numbered (1),(2) . . . (n) capable of bonding with 1,2 or n different antibodies. This is schematically represented on FIG. 8 where the first antibody is indicated as AB1, the second antibody as AB2 and a two-site antigen as (2)AG(1). In this case, it is assumed that the antigen is not detectable per se optically whereas AB2 is detectable after reacting on the appropriate second site of AG. Thus, in this case in which (2)AG(1)? is to be determined, a core is used with an initial reference coating of a first antibody (AB1) and is contacted with the antigen solution. The latter will thus bind to the core by its first binding site after which the second antibody AB2 in reference amount is added and its rate of binding on site 2 of the antigen is measured in view of the optical changes occurring in the core as the result of this binding. Of course in this procedure, the first reaction AB1+(-1)AG(2) can be allowed to go to equilibrium before adding the reference quantity of AB2; or, alternatively, a simultaneous type test can be undertaken, i.e. the AB2 can be added to the solution simultaneously with the contacting thereof with the AB1 coated guide core. This is particularly applicable where $AB_1$ and $AB_2$ are different monoclonal antibodies (see for example, UOTILA et al. Journal of Immunological Methods 42 (1981) 11-15). Also, any variations of the afore described assay system can be adapted by those skilled in the art without departing from the spirit of the invention, the operating parameter of any of such variation being defined with reference to calibrating solution samples of the analyte.

Figure 9:
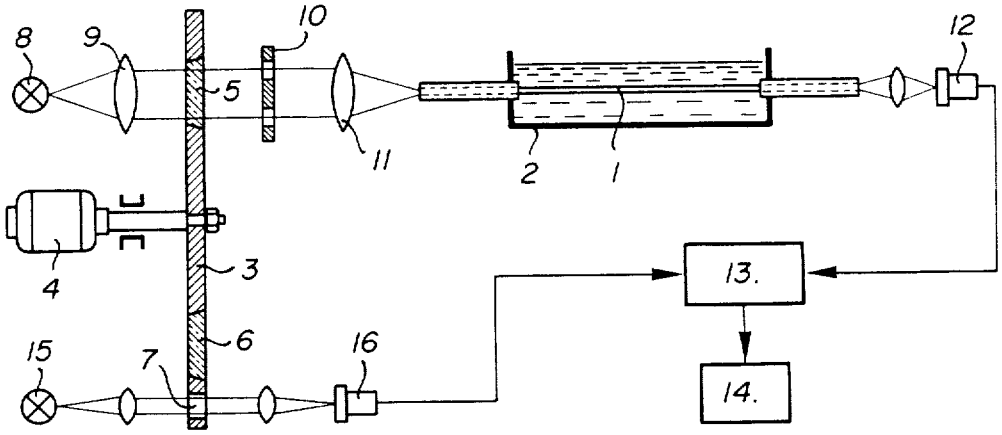
FIG. 9 is a schematic representation of an apparatus for measuring in situ changes in the light signal travelling through an optical fiber caused by the deposition of a complex film on said optical fiber.

Examples of devices for carrying the various embodiments of the method of the invention in the fields of optical absorption, fluorescence and scattering as well as ellipsometric measurements will now be presented with reference to a subsequent part of the accompanying drawings in which, The apparatus shown schematically in FIG. 9 essentially comprises the following components:

(a) A fiber optic 1, the central part of which passes through a container or cuvette 2 for holding a liquid analyte to be determined; the cladding of the fiber section immersed in the liquid has been removed so that this section can be coated, before operation, with a thin film of a specific complexing reagent of the species dissolved in the liquid and which should be determined. The assembly of the fiber 1 and the holder 2 constitutes the test probe of the apparatus.

(b) A chopper disk 3 rotated by a motor 4 and provided with two diametrically opposed windows with filters 5 and 6, plus a hole 7.

(c) A main light source 8, a collimating lens 9, an annular aperture 10 and a focusing lens 11 for injecting into the probe fiber core an angularly selected light beam. In this particular embodiment, the fiber is multimode and the aperture 10 is arranged for passing specific modes according to some requirements to be discussed hereinafter. However, with modifications to be further discussed later the present apparatus can also be used in conjunction with lower mode fibers, e.g. single mode. The focussing lens, represented schematically on the drawing is actually an optical system analogous to a microscope objective but which can be adjusted, in addition to its displacement along the optical path, sidewise and up and down for accurately positioning the beam in front of the fiber front end.

(d) Then, the apparatus comprises a main light detector 12 for transforming the exit light signal from the core into an electric signal, a lock-in amplifier 13 and a display device 14. A reference signal is also provided by another source 15, the light of which is pulsed by passing through hole 7 of the chopper and directed to a detector 16, said detector then applying corresponding electric pulses to the lock-in amplifier 13.

Figure 10A:
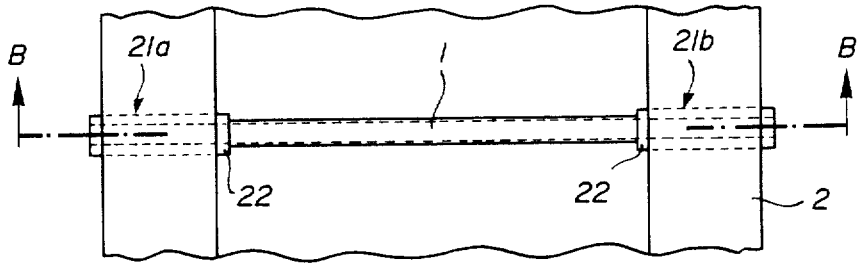
FIG. 10a is a partial top view of said probe.

One embodiment of an analytic probe usable with the present apparatus is depicted on FIG. 10 (FIGS. 10a+10b) which shows a plastic holder tank 2 in two opposite sides of which S shaped grooves or slots 21a and 21b have been cut. A portion of a fiber optics 1 with its cladding 22 has been inserted into and is being held by said grooves. The cladding of the middle portion of the fiber has been removed, for instance, by etching with a suitable solvent, and thereafter coated with a thin fim 23 of a specific complex conjugate of the species to be determined, such species being represented by the small squares 24.

The description of the operation of the present device then follows: Filter 5 is first selected for passing through the core a wavelength $\lambda_1$ which is modified by absorption at each internal reflection site because of absorption of part of the evanescent wave by the coating of the complex material that will form between the film 23 and the dissolved molecules to be analyzed 24. For illustrative purposes, it may be said that 23 represents a very thin layer of an antibody (AB) and 24 represents molecules of a specific antigen (AG) to be determined, the assay being of the "direct type" kind illustrated on FIG. 4. Filter 6 is selected for passing a wavelength $\lambda_2$ through the core that is essentially not absorbed by such complex coating and hence not affected by the immunological reaction involved. Thus, when the chopper 3 rotates two signals $\lambda_1$ and $\lambda_2$ are alternately fed to the probe core, one signal $\lambda_1$ that will be progressively absorbed with growth of the coating 23+24, and another signal $\lambda_2$ which will serve as a reference signal i.e. for calibration and compensation purposes (cell or fiber replacement, etc.). The probe is prepared by selecting a suitable length of optical fiber (multimode in the case shown on FIG. 10), inserting it into the grooves 21a and 21b so that the middle portion is held horizontal in the cuvette 2; water tightness is provided by then filling the grooves with a rubber grout or cement solution and allowing it to dry. Then the cladding of said middle portion is etched away. For a resin clad fiber, this is done with a suitable organic solvent for this cladding; for a glass clad fiber, the etching is performed with dilute hydrofluoric acid. In this last case, it is not necessary that the cladding be etched completely for reasons explained below. Then, after the dissolving or etching solution has been removed and the cell cleaned thoroughly with distilled water, the fiber core is coated with a film of antibody (AB) by usual means, i.e. by filling the cell with an AB solution so that AB deposits onto the core as a uniform layer (if, by any chance, the surface of the fiber has not sufficient affinity for the molecule to be deposited thereon, it can priorly be made bonding by the special treatments known in the art, e.g. grafting bonding sites, applying an intermediate reactive layer, etc.. In this respect, an abundant literature exists on the subject (as disclosed in European Patent Application No. 29411). After the emptying the cell and rinsing, the latter is mounted on the apparatus at the place indicated between the lens 8 and the detector 12 and a suitable buffer solvent is introduced therein. The apparatus is then activated and the chopper is rotated at a convenient speed, e.g. 120 rpm. The signals $\lambda_1$ and $\lambda_2$ are fed to the core of the probe and the detector 12 converts them into approximately squared electric pulses which are fed to the lock-in amplifier 13. A reference locking signal is also provided once every turn, via the hole 7, by source 15 and detector 16 enabling the amplifier to distinguish (by coincidence) between the pulses from $\lambda_1$ and $\lambda_2$. In practice, the controls are preferably set up so that the said pulses have about the same magnitude before starting the reaction. Then, at zero time, the sample to be analyzed (a solution of AG) is added to the cuvette of probe 2 and mixed rapidly with the buffer (for instance with a stirrer or a gas bubbler not shown). The signal due to $\lambda_1$ then starts to progressively change at the exit of the core of the probe, as a consequence of the molecules of the analyte AG binding to the fiber core (for building the AB.AG complex) and said complex absorbing a part of the evanescent wave energy of $\lambda_1$, at a rate proportional to the concentration of AG, corresponding variations being provided to the amplifier in the form of the corresponding electric pulses from the detector 12. Thus, the computing circuits associated with the lock-in amplifier 13 will compute the data resulting from the ratio of the $\lambda_1/\lambda_2$ signals and provide the results to the display system 14, for instance in the form of a rate curve recorded on a chart (of course, any other type of display can also be used if desired; digital or oscilloscope, etc.). The obtained rate data are thereafter compared to standard data obtained from solutions of AG of known concentrations and the unknown concentration is provided by interpolation. Such calculations can be made manually or can be done automatically by means of a microcomputer, the reference data being stored in the memory thereof. By selection of appropriate periods during the time course of the reaction, the desired reaction rate data can be selected and distinguished from other rate data due to the reaction of interfering and undesired reactions proceeding more or less simultaneously but at different rates. Additionally or alternatively, the equilibrium conditions can be derived by extrapolating and by this the time taken to do each measurement in comparison with normal equilibrium measurements is reduced. Further consideration about this question can be found in "Kinetic Versus Equilibrium Methods of Analysis" by B. W. RENOE et al., in "Centrifugal Analysis in Clinical Chemistry, PRICE & SPENCER; PRAEGER (1980) and Analytical Chemistry 50/02, (1978), 1611–1618.

It is useful to note at this point that the sensitivity of the measurements can be varied depending on the light mode orders applied to the fiber input, i.e. changing the aperture 10 annular setting and width. This is easy to understand when it is remembered that the absorption phenomena pertaining to a totally reflected beam inside of a core and due to a cladding outside said core only affect the evanescent wave component of said beam, i.e. the electric components penetrating into the cladding. Thus, the total reflection angles of the modes selected must be shallow enough with regard to the fiber axis to ensure full reflection (even when the refractive index of the aqueous solution is slightly modified by the growing of the coating surrounding the fiber core) and steep enough to provide a sufficient density of reflecting sites along the fiber (indeed, it is only at such sites that the evanescent wave is interacting with the complex coating). Thus, a test sensitivity optimization can be reached by properly adjusting the aperture parameters, this being dependent on the respective core, test solution and complex refractive indices. Such adjustments can be determined by thos skilled in the art for each type of measurements and can be then design incorporated for the intention of field operators.

It is also interesting to note that by changing the settings of the aperture 10 parameters, the present apparatus can be made to operate in a different "class". For instance, by properly adjusting such aperture, the apparatus can be made to operate with light modes in the near vicinity of the critical angle of total $\theta_c$ for the starting system considered. Then, in the case when in the course of the test the difference $\Delta n = n_1 - n_2$ shall decrease with complex formation, the angle of total reflection at the core-coating boundary will change such that some of the modes (or all) will be suddenly refracted outside the fiber and sharp cut-off of the signal will occur. Such arrangement will therefore provide utmost sensitivity for very small amounts of analyte molecules. It is however less well adapted to quantitative measurements.

It has been said above that, when using a glass clad fiber optic, such cladding need not be entirely etched away for the present use. Indeed, since during operation, the evanescent wave will actually penetrate the cladding a few tens of nm, a residual glass cladding around the core with a thickness below that necessary for the evanescent wave to significantly interact with the reaction materials is still possible which imposes less stringent control conditions on the etching operation. Also, thicker fibers are less fragile than thinner ones.

Figure 11A:
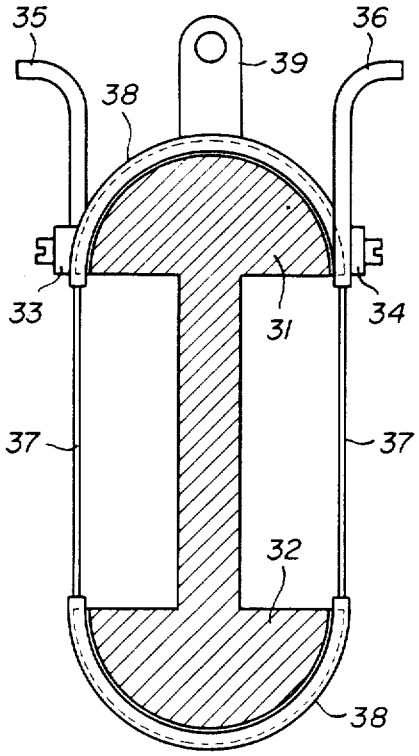
FIG. 11a is a front view.
Figure 11B:
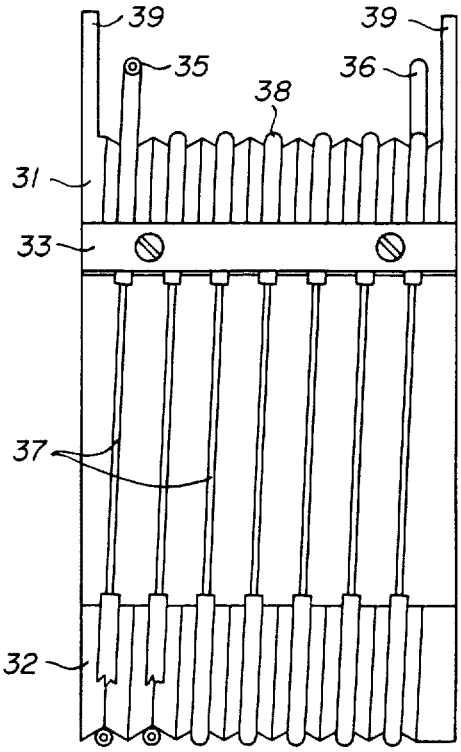
FIG. 11b is a side view.

A thick of fiber holder that will multiply the sensitivity of the test by a large factor is pictured schematically on FIG. 11a and b. This holder consists of two helically grooved flanges made of an inert plastic (plexiglass or polyester for instance) on which a piece of optical fiber is wound and clamped by clamps 33 and 34. The front and back ends of the fiber, respectively 35 and 36, are bent sideways so as to be usable with the light injecting lens 11 and detector 12. The middle straight sections of the windings 37 of the fiber are bare while the remaining curved sections 38 resting in the grooves keep their original protective cladding. The etching of the bare portions is done by first covering the lower flange of the holder with a suitable silicone rubber cement solution and letting it dry. Thereafter the holder is immersed in an etching solution down to the lower face of the upper flange whereby all the intermediate sections of the cladding will be removed, the lower rubber protected flange remaining untouched. For doing the tests and after coating the bare portion of the fiber with AG or AB as before, the holder is correctly positioned with the aid of a hook 39 in the optical path of the apparatus. Then a cuvette with the reaction medium is brought in from below, the reagent is added and the measurements are done as before.

It should be pointed out that all the above discussions on the present invention concerned the use of fiber optics to be used in an aqueous or organic medium the refractive index is near to that of water (i.e. around 1.3) whereas the index $n_1$ of the glass core of the fiber is rather near to 1.5 and the index $n_2$ of the active coating is in between i.e. $<1.5$ but $>1.3$. This condition is essential here since if $n_2$ were $>n_1$ the light would be refracted into the cladding, then back into the core and so on. As we have been before, such method is not impossible per se, for instance, it has been disclosed in Nature 257 (1975) by HARDY et al who worked with glass rod waveguides and had to use rather thick polymer coatings containing, embedded, some reagents to be determined, but it would not be practical in the present case since the surrounding solutions always have refractive indices smaller than the fiber core $n_1$ and only very thin coatings (of the order of a few Angström to a few tens of nm) are involved. In contrast, HARDY et al operated in air and did not measure rates of reactions.

Another important point that should be discussed is the question of mono-mode fibers. Indeed, with very minor modifications known in the art and mainly pertaining to light injection into the fiber, single-mode fiber optics can be used as well in the present method. Such fibers generally have a very thin core (a few microns) surrounded by a relatively thick cladding and their transmission is strongly wavelength dependent, e.g. a fiber with only 5% attenuation per meter at 850 nm may have attenuation of about 40% at 800 and 900 nm (see T. G. GIALLORENZI in Proceedings of the IEEE 66 (1978), 748). Now, for mono-mode conduction in a fibre at wavelength $\lambda$ the following expression $V=8.9a\sqrt{n_1\Delta n}/\lambda$ must have a value below 2.4 ($\Delta_n=n_1-n_2$ and a is the fiber radius in microns). Above $V=2.4$, the fiber is no longer single-mode. When the value V is small e.g. below 1), the guided single mode becomes more loosely bound, i.e. the field spreads considerably beyond the physical core of the fiber (e.g. two or three times the core diameter). Thus, the transmission characteristics of single-mode fibers are very sensitive to tiny changes ($\Delta_n$ changes) in the refractive index of the cladding, i.e. that of the organic coating which forms during the test of the present invention. Indeed, this refractive index is the key variable involved in the present assay performed with single-mode fibers as the thickness of the complex layer grows during the reaction. Whereas internal reflections in a multimode fiber allow the evanescent wave in the immediate vicinity of the reflective boundary to pass parallel to the core for a very short distance (which can be defined by Maxwell's equations) at each reflection, the mono-mode fiber allows for the passage of this evanescent wave fraction parallel to the core along the whole effective length of the fiber. Thus, the use of single-mode fibers in the present apparatus facilitates an increase in sensitivity as compared with multi-mode fibers.

Single-mode fibers can be used without etching the original cladding completely since the guided light fields extend significantly into the cladding and also into the complex layer formed during the reaction.

The modifications which must be made to the apparatus when using single-mode fibers are essentially of an optical nature, i.e. injection of the light into the fiber and detecting the signal. Such optical variations are not described here as they are known from people skilled in the art and well described in the literature (see for instance the above GIALLORENZI article and the references therein).

The present apparatus can also be used for performing the method of the invention but using fluorescence effects instead of absorption or refractive index changes. For doing this, the following modifications should be made thereto:

(a) A fluorescent labelled antigen (AG*) will be added to the analyte AG. Thus, the method will operate under the conditions of "limited reagent" immunuassays as discussed hereintofore (see FIG. 5).

(b) Filter 5 will be selected for a $\lambda_1$ specific of the excitation to the fluorescence to be measured and filter 6 will be selected for blocking $\lambda_1$ but passing the fluorescence emission wavelength $\lambda_2$.

(c) An additional filter of optical characteristics identical with filter 6 will be inserted between the fiber back-end and the detector 12.

Figure 12A:
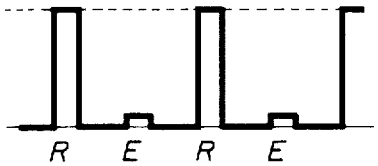
FIG. 12a concerns the situation before the reaction is started.
Figure 12B:
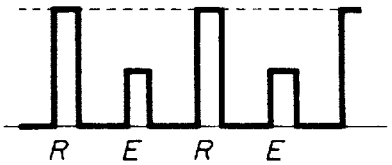
FIG. 12b concerns the situation some time during the test.

Then, the probe with buffer medium and its fiber optics 1 coated (as usual) with an AB film will be installed and the apparatus will be adjusted for response as shown diagramatically in FIG. 12a. In this figure, there is shown a succession of pulses from the detector 12; the pulses marked R are the reference pulses produced when filter 6 is in the beam; the pulses E are the emitted fluorescence pulses injected into the fiber by the fluorescent complex AB.AG* molecules that form onto the fiber core. Thus, at the start, the E level (FIG. 12a) is about zero from no fluorescence or only residual back-ground noise. Then, the analyte containing the antigen to be determined plus a known quantity of fluorescent labelled AG* is added; a fluorescent coating gradually forms at a rate proportional to the AG concentration and an emission fluorescence signal appears in the fiber and progressively increases with time as shown on FIG. 12b. This variation is detected, applied to the amplifying and computing sections of the apparatus and recorded as the rate measurement desired. Then, afterwards, visual or computerized comparisons are made of the recorded data and standard reference data from which the desired analytical results are obtained using the techniques specific to "limited reagent" assays discussed above.

In the present embodiment, the fluorescence generated by the coating outside the fiber core is substantially reinjected into the fiber and provides the signal used for the test. A related phenomenon has been recently described (see The Journal of Cell Biology 89, 141-145 (1981) with regard to a glass block.

When using a fiber optic advantage can also be taken from a great sensitivity as the useful length of the fiber can be made quite significant although confined in a very small space and using very small volumes of solutions. It should also be mentioned that the measure of the fluorescence of coatings in immuno-assay has already been reported (see M. N. KIRONICK et al, Journal of Immunological Methods (1975), 235-240). However, in such case, the fluorescence was measured through the antibody solution and only one internal reflection site was used which gave poor sensitivity since only a very limited portion of the total fluorescence emission could be processed. In the case of using fiber optics like in the present invention, sidewise fluorescence pick up can also be measured, for example, by using a flat-coiled piece of fiber and placing the detector axially to the coil thus collecting a large part of the fluorescent light emitted by the fiber.

The present embodiment provides many advantages over the present testing methods an devices known in the art. For instance, (a) The sensitivity being proportional to the length of the immersed fiber section, very sensitive probes can be made although having small dimensions.

(b) Measurements can be made over a wide range of wavelengths, in the visible, UV and IR bands.

(c) A wide variety of substances (biological or non-biological) can be tested among which one can cite drugs, haptens, enzymes, peptides, proteins, hormones, bacteria, virsus and cells. A more complete list of detectable analytes can be found, for example in U.S. Pat. Nos. 3,817,837 and 4,299,916.

One interesting specific case is when testing blood samples for transfusion with regard to possible antibodies in the recipients blood. Thus, optical fiber probes can be prepared with a film containing the blood constituents of said patient and test against the blood cells of potential donors. In case of cross-reactivity, the cells will precipitate onto the fiber (because of the reaction of their own AG centers with the AB of the fiber) and this reaction can be easily monitored by one of the typical absorption bands of hemoglobin (e.g. at 555 nm). Another interesting specific case is the possibility of using a waveguide sensor in vivo to make qualitative or quantitative measurements of analytes within or secreted from the body. For example, in diagnosis, it would be possible to assay the quantity of circulating insulin in response to a glucose loading test and, in treatment with injected hormones, the in vivo sensor would detect the circulating hormone concentration. The posibility of using in vivo sensors has now been described by BUCKLES, but the present invention would have the added advantage of absence of a label in the immunoassay mode (where many labels are highly active compounds with possible toxic or carcinogenic effects) and improved light transmission thus obviating the need for special transmission fibers to couple the signal in and out of the sensor as described by BUCKLES.

The apparatus shown schematically on FIGS. 13a and 13b comprises the following key components:

An optical probe composed of a slanted edge waveguide plate 41 held by brackets (not shown) and a counter plate 42 maintained in accurately controlled parallel facing relationship in respect of the wave-guide 41. The plate 41 can be made of high quality float glass accurately cut or quartz. The plate 42 can be a microscope slide. The space 41a between the plates 41 and 42 is of the order of a fraction of mm; this ensures that an analyte solution can be easily introduced into this space wherein it will be held by capillary forces. The apparatus further comprises a light source 43 (in this particular embodiment, the light source is a He-Ne laser providing polarized light), a chopper disk 44 actuated by a motor 45 and provided with a hole 46 for providing a pulsed light signal to be sent toward the optical probe through an optical system comprising focusing lenses 47 and 48, a mirror 49, a polarizer plate 50, a cylindrical lens 51 and a diaphragm 52 for minimizing stray light. The reason why the light signal is pulsed is to provide for ultimate phase sensitive amplification of the detected signal.

The apparatus further comprises a photomultiplier detector 53 with its high voltage power supply 54, the outlet of which is connected to a lock-in amplifier 55 through a two way switch 56. The photomultiplier is arranged to collect the light scattered by the product that forms on the waveguide plate in the space 41a as the result of a chemical reaction occurring between a reactant and an analyte of the solution filling space 41a. The scattered light is indicated by arrows 57.

The apparatus further comprises a detector 58 for collecting the light emerging at the output of the waveguide core after multiple reflections therein as shown on the drawing. The output of this detector can be alternatively fed to the lock-in amplifier 55 through switch 56. The references signals for the apparatus are provided by a semi-transparent mirror 59 which derives a small portion of the light of the source on a detector 60, the latter providing an intensity reference signal fed to an analog divider 61, this being for compensating possible variations of the source during the measurements. A pulsed locking reference signal is provided by a mirror 61 and a detector 62, the corresponding electric signal being fed to the amplifier 55. The apparatus finally comprises and electronic unit 62 which will comprise a display element (like in the previous embodiments) and recorder for recording the output data and, optionally, a microprocessor for computing the measured data and effecting the required comparisons with the stored reference data from calibrating experiments.

In practice, the present apparatus is operated as follows. The first step is to prepare the optical probe by depositing a film of a reactive species on the face of the waveguide 41 that defines the space 41a. Details on how to do this are given hereinafter. Then the guide 41 and the plate 42 are mounted on the apparatus and the optical and electronic systems are started up. After a few minutes of warming up, the controls are adjusted for zero response from photomultiplier 53 (or alternatively, full transmission from detector 58). Then the analyte solution (a few $\mu$l) is pipetted into space 41a whereby the analyte in solution begins reacting with the reactant film on the guide 41. When the analyte-reaction product furnishes scattering sites (large molecules, agglomerates, etc.) a scattered signal reaches the photomultiplier tube 53 which is amplified, processed and displayed with time by the display included in the unit 62. This results in a rate cuve; the slope data are recorded and conputed against standard data obtained from calibrating samples and tored in the memory of the electronic unit 62. This computation provides the desired analytical results (e.g. the concentration of the unknown species in the analyte solution) according to usual means. If the output of detector 58 is not used, the edge 41b of the guide 41 can be masked to minimize the formation of back scattered light. Masking can be done for instance with black paper or paint.

An improvement to the aforedescribed embodiment is illustrated on FIG. 14. Instead of using a perfectly homogeneous working surface for the waveguide 41, one can first treat that surface to provide discontinuities thereon. For instance, one can modify the inherent adhesiveness of the surface toward the reaction according to a certain pattern (achievable for instance by the known photolithographic techniques). In the case represented on FIG. 14, the surface 41c of the guide 41 has been slightly roughened at areas indicated by numeral 41d, such areas being as parallel stripes about one wavelength wide and separated by a distance of the same order of magnitude. Such a grating-like pattern can be obtained by first covering the surface with a photoresist, exposing said resist layer through a photographic film with the negative image of the grating, developing (i.e. dissolving the unexposed areas in a suitable solvent)

and etching slightly the bare areas, after developping, for instance with HF. After final removal of the resist, the plate has a grating pattern of stripes with alternating zones of higher and lower affinity for proteins (antigens or antibodies). Thus, when the plate is contacted with a reactant (AB), the latter will mainly attach to the etched areas as indicated on FIG. 14 by the letters AB. At this stage, the thickness of the pattern is not sufficient to provide scattering; however, in the presence of the antigen (which is of the proper nature to scatter light), the latter will bind to the stripes having thereon the antigen i.e. as indicated by AG on the drawing. This discontinuous type of layer will provide distinct orders of diffracted scattered light in contrast to the stray scattering mode of the main embodiment thus improving the directivity and the collecting efficiency (by the photomultiplier tube) of the scattered signal. In FIG. 14, the arrows 65 indicate the zero order of diffraction and the arrows 66 indicate the first order of diffraction. By collecting a specific order (e.g., the first) the collection of the signal by the photomultiplier tube 54 is then strongly amplified and the signal-to-noise ratio is increased in this modification as compared with the collection of the stray scattered light which is only around 10% of the total scattered light.

Figure 15:
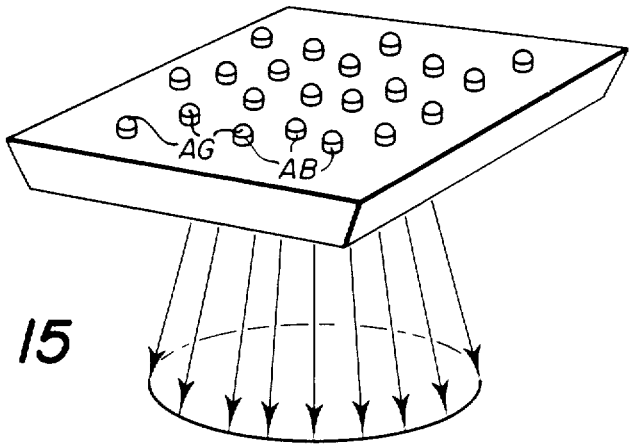
FIG. 15 represents schematically part of another modification of said embodiment.

In another modification, see FIG. 15, a perfectly flat and regular surface 41c of a waveguide was sprayed with microdroplets of antibody (AB) and, during analysis, the antigen AG attaches only to such preferential areas. Such a structure constitutes a statistical scatterer which scatters light in the shape of a cone the size and geometrical parameters of which depends on the size and the distribution of the droplets. Thus, also here, there is a directional effect that contributes to increase the efficiency of the signal collection. Another advantage of providing diffracted light signal is to minimize the importance of accidental scatterers such as dust particles or scratches in the glass with larger sizes (of the next higher order of magnitude, i.e. about 10λ or more); in such case the angle of diffraction is smaller and, the resulting diffracted light not reaching the photomultiplier tube, its presence can be neglected.

Figure 16:
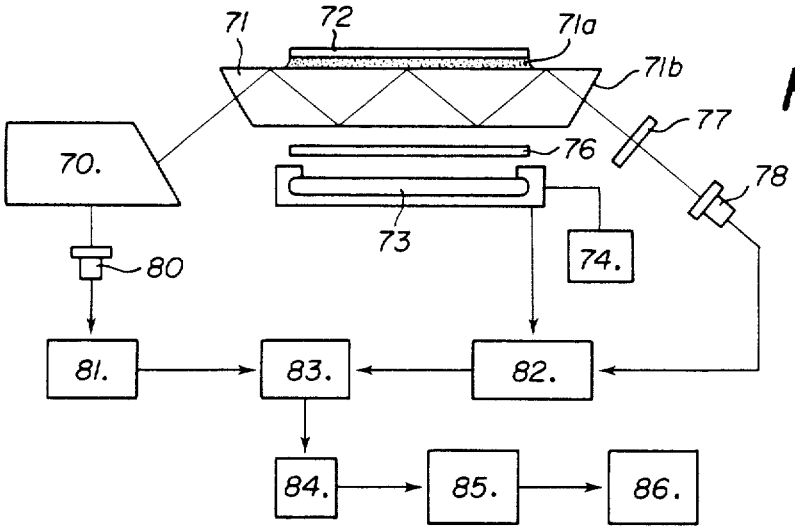
FIG. 16 represents schematically an apparatus for measuring optical changes caused in a wave-guide to fluorescence phenomena.

The apparatus represented on FIG. 16 is generally similar to that already discussed with reference to FIG. 13 but it is adapted for fluorescence measurements instead of scattered light measurements. This apparatus essentially comprises an optical system represented by block 70 which is practically identical with the system used in the apparatus of FIG. 13. Therefore, the details are not repeated for simplication. This system 70 contains a pulsed light source and means for providing a test signal of the correct excitation wavelength properly directed to a waveguide 71 and a reference signal to a reference detector 80. Like in the other embodiment, there is a plate 72 determining with guide 71 a thin space 71 for introducing the analyte solution, the layer of reactant being coated on the upper face of the guide 71. The apparatus also comprises a side-detector (the photomultiplier tube 73 and its supply 74), a core output detector 78 and blocking filters 76 and 77 (these items are missing in the previous embodiment). The electronic components of the apparatus comprise two integrator amplifiers 81 and 82, a multiplexer 83, an analog to digital converter 84, a microprocessor 85 and a display recorder 86. All these elements are conventional and their operations are familiar to those skilled in the art.

The operation of the apparatus in the side-pickup mode is quite similar to that described for the scattering embodiment. Thus after preparing the waveguide 71 with a layer of reactant on its upper surface and the plate 72, the analyte solution is introduced to provide a fluorescent reactant-analyte product. The optical unit 70 sends a test signal of the proper wavelength $80_1$ for exciting the fluorescence of wavelength $\lambda_2$. The emitted fluorescent light goes across screen 76 (which screens off all other wavelengths including scattered exciting light) and hits the photomultiplier tube 73 whereby a signal proportional to the fluorescence (and to the extent of the reaction) is produced. This signal, together with the reference signal from detector 80 is fed to the multiplex amplifier 83 which alternatively feeds them to the remainder of the electronic elements whereby a processing similar to that described previously will occur.

Figure 17:
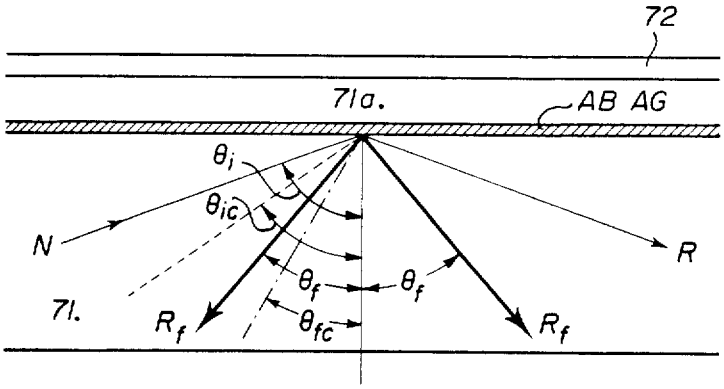
FIG. 17 represents schematically on a much exaggerated scale a portion of the apparatus of FIG. 16 to show the angles of reflection of the incident and fluorescent light involved.

Simultaneously or alternately with the aforementioned operation, the signal occurring at the core output and falling on detector 78 can also be monitored. For understanding how this is possible, reference is made to FIG. 17. On this figure, there is shown a portion of the guide 71, the plate 72 and, in between the space 71a and, schematically, a layer of AB.AG product (the product which is the result of the reaction of the reactant AB plus the analyte AG of which the rate is being measured in the test). The figure also shows the various light beams involved in the excitation to fluorescence process, i.e. N is the incident beam at $\lambda_1$, R is the reflected beam of wavelength $\lambda_1$ and R, are the generated backward and forward fluorescent beams ($\lambda_2$). $\theta_i$ is the angle of incidence and $\theta_{ic}$ the crical angle for $\lambda_1$. $\theta_{fc}$ is the critical angle for $\lambda_2$. Now, as represented, the excitation light N hits the internal surface of the wall at an angle $\theta_i$ larger than the critical angle $\theta_{ic}$ and it is thus reflected (R). However, part of the evanescent excitation wave is absorbed by the AB.AG layer and energy is reemitted at a shorter wavelength $\lambda_2$. Now, by virtue of the reciprocity principle (confirmed quantitatively by C. K. CORNIGLIA et al. in J.O.S.A. 62, (4), 1972, 479–486), excited molecules emit evanescent photons which behave exactly as the incident evanescent wave photons. Thus, the fluorescence emitted by molecules close to the dense-to-rare interface (the AB-AG layer) propagates into the dense medium at angles larger than the critical angle $\theta_{fc}$ for $\lambda_2$. Actually, peak fluorescence is observed when $\theta_i$ is close to $\theta_{ic}$ and at angles close to $\theta_{fc}$ (see R. E. BRENNER et al., Fiber Optics, Advances in R & D, Providence, RI, USA; 19–23 June 1978, NY Plenum Press (1979)). Thus, the emitted fluorescence maximum intensity concentrates within a relatively small angular range and, when guided in the waveguide, the output at several interaction sites add up to provide a higher intensity signal at the output of the core. A second point of importance is that, because the refractive indices are different for different wavelengths, the exciting signal and the fluorescent signal are following paths with different reflection angles in the guide and they will emerge from the output also with angles different from one another. Hence, there is an inherent optical separation of the emitted beam from the excitation beam at the output of the core and detector 78 can be suitably placed to be in the path of the fluorescent signal ($\lambda_2$) while avoiding the residual excitation beam ($\lambda_1$) even in the absence of filter 77.

Figure 18A:
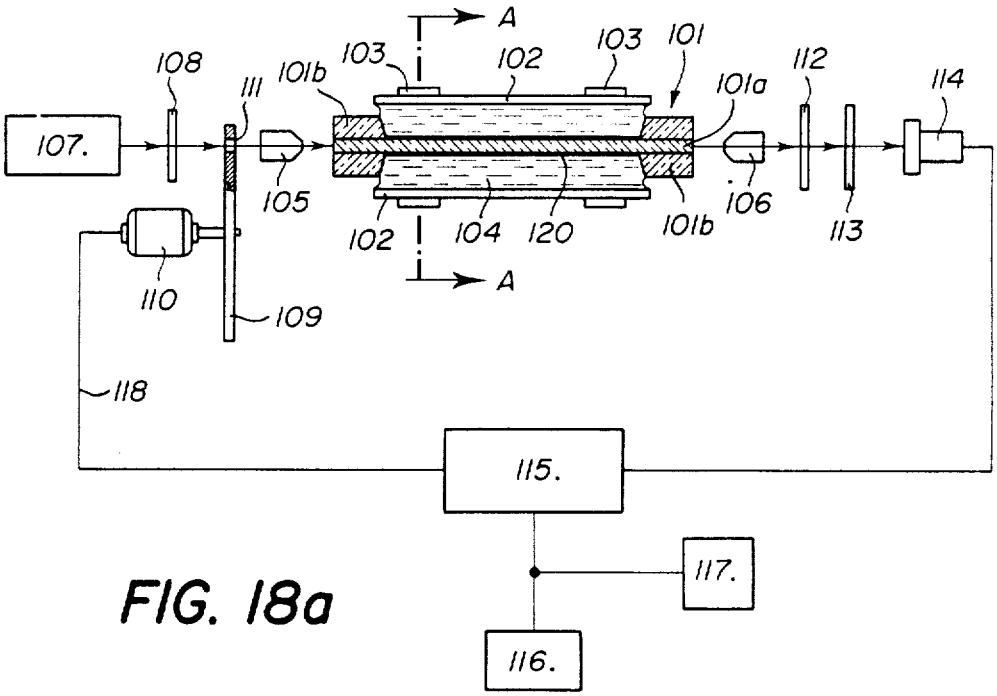
FIG. 18a represents schematically (top view) an apparatus for measuring ellipsometrically optical changes in an optical fiber caused by the formation of a complex film on said fiber.
Figure 18B:
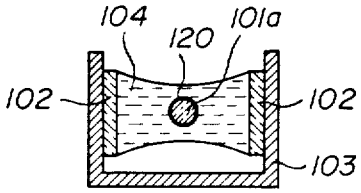

The apparatus represented on FIGS. 18a and 18b is intended for measuring optical changes occurring in an optical fiber waveguide provided by the formation of a product on the surface of said fiber, this measuring being performed by means of ellipsometry. Ellipsometric measurement applications to bioassays have been detailed in our related European application EP No. 81 810 255.0 and the present reader is referred to this disclosure for general considerations in this field. The main difference of the present application with the prior disclosure is the use of an optical fiber instead of the generally known flat reflecting surfaces. Ellipsometry is based on the measurement of changes in the degree of elliptical polarization of light caused by the presence of a film of matter deposited on the reflecting surfaces. In view of the particular nature and geometry of optical fibers as compared to flat surface waveguide, additional features must be considered. Firstly, in order to maintain a beam of light linearly polarized in a fiber, one must use a special family of light modes. These modes are defined as the $HE_{lm}$ modes, with $m=1,2,3 \ldots n$ (n being limited by the size and refractive index of the fiber considered, see E. SNITZER and H. OSTERBERG J. Opt. Soc. Am 51, 499 (1961)). Secondly, to be able to measure the full extent of any polarization modification caused by a reaction occurring on the surface of the fiber, it is important that signals with any direction of polarization be transmitted equally well along the wave-guide. Thus, geometrical perturbation such as that caused by mechanical stress on the fiber should be avoided because, in such case, one particular direction of polarization could be favored. Consequently, in the present apparatus, the optical probe (of which the key component is the optical fiber) is made short and rigidly immobilized to minimize the undesirable effect of vibration or other possible perturbations.

In order to preferentially excite the $HE_{lm}$ modes in an optical fiber, the radial light intensity should have a Gaussian distribution, e.g. that obtained from a laser radiating in the fundamental mode and the beam should be directed axially and centrally on the fiber end. This coupling can be achieved by means of a microscope objective. Now, for minimizing background perturbations, it is preferable to operate with only one mode rather than several modes simultaneously. In the present apparatus, the $HE_{11}$ mode (lowest single mode) was selected for simplicity. In principle, multi-mode fibers are usable with single mode signals. This can be made possible (i.e. the proper Gaussian distribution can be selected) by letting the incident beam diameter at the fiber input face be 0.65 times the diameter of the fiber core. However, this is not really satisfactory because other modes with various polarization states are also excited to some extent and a partially depolarized signal is obtained at the probe output. Hence, it is greatly preferable to use a single-mode fiber in this embodiment since this will essentially only transmit the $HE_{11}$ mode whereby no conversion to higher order modes and thus no decay in the degree of polarization will occur. Consequently, a higher signal-to-noise ratio is obtained as compared with using multi-mode fibers.

In the present embodiment, the fiber length is preferably 10 cm or less for the aforementioned reasons. It is preferably a high quality single-mode fiber with respect to depolarization and birefringence characteristics. Fibers obtained by CVD techniques such as that disclosed in H. AULICH et al., Applied Optics 19, 22, 3735 (1980) are preferred.

The apparatus represented on FIGS. 18a and 18b comprises an optical probe comprising a partially etched piece of optical fiber 101 with a core 101a and a symmetrically removed cladding 101b. The technique for removing the cladding is the same as that disclosed for other optical fiber applications in this specification. At a very short distance from the bare fiber core (a fraction of a mm) on both sides thereof are placed two glass plates 102 rigidly maintained on "U" shaped brackets 103. The clad end portions of the fiber waveguide are clamped by means of clamps not shown mounted on an adjustable rack not shown, the latter enabling the position of the fiber to be accurately controlled sidewise and up and down. The space 104 between the fiber core and the plates 102 is the reaction site, the liquids to be tested being retained by capillary forces between the fiber and the plates.

The present apparatus further comprises two microscope objectives 105 and 106 for coupling the input incident beam with the fiber and the output elliptically polarized signal with the detecting system, respectively. The incident beam is generated by a light source 107, (in this embodiment a He-Ne laser) the output light of which goes across a polarizer plate 108 and a rotating chopper disk 109 driven by a motor 110 and having a hole 111 for chopping the signal. Then, the detecting system of the apparatus comprises a quarter-wave plate 112, a polarization analyzer 113 and a photodetector 114, these elements being similar to corresponding elements described in related application EP 81 810 255.0 and operating similarly. Finally the apparatus comprises a lock-in amplifier 115 and associated components, i.e. micro-computer 116 and recorder 117, the functions of these electronic components being essentially the same as the of the corresponding elements already described earlier in this specification. It is to be further noted that the reference chopped signal used for reference purpose is represented on the drawing as originating from the chopper motor 110 and being transmitted to the amplifier 115 by a line 118.

The operation of the apparatus is very similar in essence to that described in the previous embodiments combined with the operation of the apparatus described in related application No. EP 81 810 255.0. Thus, for making a test, the bare portion of the fiber is first coated with a reactant (e.g. the antibody) as shown by numeral 120 on the drawing by filling the space with the proper solution as shown on the drawing by dashed patterns. Then after the usual rinsing and drying stages, zeroing of the instrument in the presence of a blank buffer by properly alternatively rotating the polarizing elements 112 and 113 (see description in application No. EP 81 810 225.0), and removing the blank solution, the solution to be tested is introduced for starting the reaction between the antigen analyte and the antibody coating which results in the growing of the reaction-analyte layer on the waveguide core and consequent modification of the elliptically polarized output. The corresponding change from the photodetector 114 is amplified and monitored in the electronic associated components 116 and 117 and provides the desired data exactly as in the previous embodiments.

For the immobilization of a film of antibody on a waveguide core (or, of course, of antigen if this is the antibody that must be determined) many methods known in the art can be used as already mentioned hereinbefore. In carrying out the present invention, with reference to immunoassay testing, it is generally preferred to take advantage of the fact that most types of glass will strongly adsorb proteins via their hydrophobic or hydrophilic areas. Thus, in such case, the etched fiber is first cleaned in an aqueous detergent (e.g. a 2% aqueous detergent solution). Then, it is rinsed under running water and immersed overnight in conc. $H_2SO_4$. Then, it is rinsed with distilled $H_2O$ and dried in warm air. It then readily binds proteins from solutions, e.g. human IgG in buffers.

In another preferred method, the active portion of the guide after cleaning with $H_2SO_4$ and rinsing as above, is immersed for an hour in a 15% (w/v) of $TiCl_4$ in an anhydrous organic solvent like acetone or ethanol. Then, it is washed with distilled water and 0.1M phosphate buffer (pH 7) and, thereafter, contacted with a human IgG solution (2 g/l in 0.9% NaCl solution or 0.1M phosphate buffer, pH 7). The fiber (or rather the probe) thus made ready for testing against AG's is stored wet in a suitable buffer (or even dry for shorter periods).

SPECIFIC EXAMPLES

The Examples that follow illustrate the practical aspects of the invention.

EXAMPLE 1

An optical probe including a waveguide of the type described with reference to FIGS. 13a and 13b and a glass counter plate was prepared for undertaking immunochemical assays as follows: the glass items made of the following type of glass (n=1,523): "Farbloses Brillenrohglass B-2160, DESAG", were first washed with a warm detergent solution, rinsed in distilled water and air dried. Then, they were immersed for 5 min in concentrated $H_2SO_4$ at 95° C., rinsed in distilled water and dried with clean tissue. The subsequent manipulations were then carried out with utmost care the clean glass surfaces not being touched and the probe handled by the edges. The plates were mounted on the apparatus as illustrated on FIGS. 13a and 13b, leaving a space of 0.3 mm between them. For coating purposes an approximately (but accurately weighed) 1 g/l antigen solution was prepared by dissolving the required amount of solid human immunoglobulin (SERVA BIOCHEMICALS, Heidelberg, Germany) in 0.9% NaCl solution. About 0.2 ml of such solution was placed between the glass elements 41 and 42 of the probe by means of a syringe and allowed to stay there for two hrs at room temperature. During this time, approximately 1 to 10% of the AG available in the sample became attached to the surface of the wave-guide (about 2-20 μg). Then the cell was emptied by absorbing the liquid with absorbent material and the cell was rinsed with distilled water, the rinsing waters being removed as before. Then a 0.1M phosphate buffer (pH 7) containing 2 g/l of bovine serum albumin and 0.5 ml/l of liquid detergent (TWEEN 20) was placed in the cell and left there for 1 hr. The serum albumin would fill the "holes" left empty on the glass after coating with the antigen (i.e. since the antigen does normally not attach to all available areas on the glass and, since the antibody to be tested has also affinity for the bare glass, the presence of uncoated areas, the "holes" on the wave-guide, might subsequently introduce errors in the measurements). Since the antibody has no affinity for the bovine serum albumin, this treatment would there simply disable the unused bare portions of the glass. The detergent actually supplemnts such action.

After again washing and rinsing, the cell was allowed to dry in a current of pure warm air. It was then ready for the experiments. All analysis were done at room temperature. The various optical and electronic components, except the photomultiplier tube, were turned on and allowed to equilibrate and a sample of antibody solution (2 ml) was introduced into the cell by the same means. The antibody selected was rabbit anti-human immunoglobulin froom DAKO IMMUNOCHEMICALS, Cppenhagen, Denmark in 0.9% NaCl. The initial solution as received was a 10 g/l protein solution with a titre of 900/ml, i.e this number (provided by the manufacturer) means that each ml of the antibody solution actually neutralizes 900 μg of the antigen (neutralization here means that when such reciprocal quantities of both ingredients have reacted, the solution contains no more appreciable AG or AB). Thus, for calibrating purposes, known antibody solutions conveniently diluted were used for performing the test (see Table I). As soon as the cell was filled with the calibrating solution (n=approximately 1.33), the room was darkened to avoid saturating the photomultiplier tube and the latter was switched on. The rate curve generated from the scattered light signal picked up by the photomultiplier started to develop after some seconds of equilibration (probably due to the time necessary to properly wet the proteins of the coating). The reaction was allowed to proceed for about 21 ∝ 5 min and the slope of the rate curve (nearly linear) was averaged over that period.

The results are summarized in Table I below which gives the values of dilution of the samples of antiserum and the corresponding calculated titre values as well as the slopes of the corresponding rate curves as measured with the apparatus used.

TABLE I

| Dilution of antiserum (1 ml + ml of 0.9 NaCl) | Antibody titre of antiserum | Slope of rate curve (mV/min) |
|---|---|---|
| 1 + 20 | 42.9 | 22.0 |
| 1 + 100 | 8.9 | 12.6 |
| 1 + 200 | 4.5 | 6.1 |
| 1 + 1000 | 0.89 | 0.8 |

For the analysis of an unknown sample, the same procedure was followed, the rate data being recorded and, afterwards, compared to the standard date of Table I. The desired analytical data were obtained by plotting the analytical rate value obtained against the corresponding titre as given by said data of Table I

EXAMPLE 2

The reverses of the experiment described in Example 1 was performed with the same apparatus and under the same conditions. In this case, the waveguide in the optical probe was coated witha film of antibody (rabbit antihuman immunoglobulin) by means of 0.2 ml of the initial solution of titre 900/ml (see Example 1). All other operation were the same as described in Example 1. The calibrating samples were prepared in Example 1. The calibrating samples were prepared from known dilutions of the antigen solution as given in Table II which also summarizes the slopes of the rate curves recorded.

TABLE II

| Antigen solutions (ml/l) | Slope of rate curve (mV/min) |
|---|---|
| 0.42 | 4.9 |
| 1.63 | 11.3 |
| 5.32 | 19.0 |
| 10.16 | 21.7 |

For analyzing unknown samples of AG, the procedure already described in Example 1 was followed, i.e. the slope of the corresponding rate curve under test was measured and the value obtained was correlated with the corresponding antigen concentration by comparing with the graph prepared from the values summarized in Table II.

EXAMPLE 3

In this Example, the signal obtained from the light emerging from the back-end of the waveguide and falling on detector 58 was sued for generating the rate curve. The optical probe was essentially the same as that used in Example 2 (with a coating of AB, rabbit anti-human immunoglobulin). Samples of antigen solutions (like in Example 2) were used the concentrations of which are shown in Table III below. The remainder of the operations were carried out exactly as explained in Examples 1 and 2 with the difference that the photomultiplier 53 was not used and that the signal actually decreased as the reaction went on (this is because the proportion of light not reaching the output of the waveguide increases as the reaction proceeds). The slope of the rate curves recorded as a function of the amount of AG present in the samples is given in Table III.

TABLE III

| Antigen solutions (ml/l) | Slope of the rate curved (mV/min) |
|---|---|
| 1.0 | −0.42 |
| 0.32 | −0.35 |
| 0.10 | −0.31 |
| 0.03 | not readily measurable |

EXAMPLE 4

The following Example illustrates a competitive assay method of the type discussed with reference to FIG. 5. For this, a fluorescence measurement type of apparatus of the kind disclosed with reference to FIG. 16 was used. The optical probe was prepared by coating the corresponding wave-guide 71 with a film of human immunoglobulin (AG) by the same procedure described in Example 1. The antibody AB* used was labelled with fluorescein isothiocyanate (FITC) and specific to the antigen tested (it was obtained from DAKO IMMUNOGLOBULINS, Copenhagen). The unlabelled corresponding antibody AB was also obtained from the same source. In the following experiment, the output face 71b of the waveguide was coated with black paint to minimize scattered incident light.

In each experiment, a fixed quantity of tracer antibody AB* was added. This quantity was 100 μl of the Dako product diluted 1/200 in 0.1M phosphate buffer at pH 7 and it was mixed with 100 μl of the test solution of unlabelled AB in the dilutions given in Table IV. The operation was performed as in the previous Examples, the mixed 200 μl portions being injected between plates 71 and 72. The results are reported in terms of the slopes of the corresponding rate curves in Table IV.

TABLE IV

| Dilution of antibody (1 ml + ml of buffer) | Antibody titre | Slope of rate curve (mV/min) |
|---|---|---|
| 1 + 20 | 42.9 | 11.6 |
| 1 + 100 | 8.9 | 57.7 |
| 1 + 200 | 4.5 | 90.3 |
| 1 + 1000 | 0.89 | 95.5 |

For the measurement of unknown solutions of antibody, the same technique was used (addition of 100 μl of the labelled antibody) and the results were obtained with reference to the standard data given above.

EXAMPLE 5

The previous Example weas repeated but, this time, the output from detector 78 at the back-end of the wave-guide was monitored. Using the same tests concentrations given in Table IV, the corresponding rate results (in increasing order) were obtained (mV/min): 2.9; 4.8; 6.1; 6.6.

EXAMPLE 6

Figure 10B:
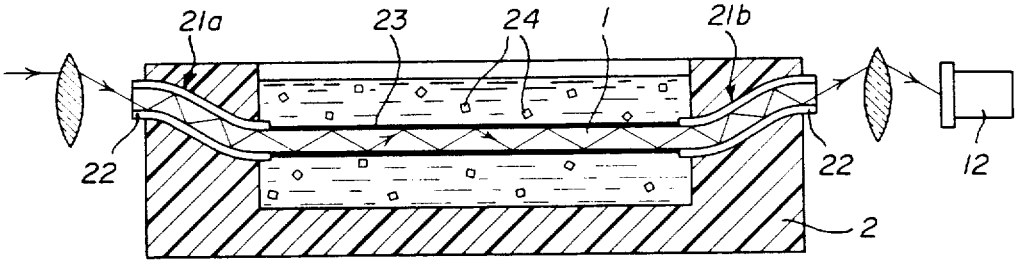

A probe cell was prepared by taking a piece of plastic clad silica fiber from "Quartz & Silice SA", type PCS Fibrosil WSF-UV series (diameter 380 μm, core 200 μm, losses 0.14 db/m at 350 nm, 97% transmission) and inserting it by its ends into the grooves of a PVC cell as pictured on FIGS. 10a and 10b. For caulking, a solution of silicone rubber cement in acetone was used. The cladding was etched away by filling the cell with concentrated $H_2SO_4$ and leaving it there for an hour, (unclad section about 10 cm long), then the fiber was made active by the first preferred method described at the last paragraphs before the Examples.

A film of human immunoglobulin G (IgG) purchased from "Serva Biochemicals", Heidelberg, Germany was then deposited on the fiber as follows: the phosphate buffer in the cell was removed and replaced by a 2 g/l solution of the IgG (10 ml) in a 0.9% NaCl solution. After 2 hrs, the antibody solution was removed and the fiber was rinsed with the buffer solution after which a 2 g/l solution of bovine serum albumin containing 0.5 ml of "TWEEN 20" (a detergent) in the 0.1M phosphate buffer was introduced and left there for one hour. Then, the cell was again rinsed with buffer and filled with fresh buffer (10 ml). The cell was installed on the optical bench of the apparatus of FIG. 9, filter 5 being selected for $\lambda_1 = 280$ nm (protein absorption) and filter 6 passing $\lambda_2 = 340$ nm (no protein absorption), then, adjustments were made in order to center the beam, have proper response of the electronic units and allow the system to equilibrate with the minimum of noise. Then, 50 μl of various dilutions of anti-serum (anti-IgG raised in rabbits purchased from "Dako Immunochemicals, Copenhagen) were added and thoroughly mixed by bubbling air through. The recorder was then started at zero time and the absorption changes at $\lambda_1 = 280$ nm were monitored for about 10 min. The average rate of change in this absorption signal was plotted and the slope was recorded in arbitrary units. The results are shown in Table V as a function of the AG concentration.

TABLE V

| AG (anti IgG) concentration (μg/ml) | Slope of the rate curve (mV/min) |
|---|---|
| 4.5 | 2.23 |
| 2.3 | 1.02 |
| 1.5 | 0.78 |
| 0.76 | not readily measurable |

EXAMPLE 7

The method was essentially as described in the foregoing example but replacing the rabbit IgG by a corresponding labelled anti-serum. The labelling compound was fluorescein-isothiocyanate "isomer-1" (FITC) and the labelled antiserum was obtained from "Dako". This material strongly absorbs at 492 nm (this wavelength is actually also that which excites fluorescein). In the experiment, filter 5 was selected for a $\lambda_1=492$ nm filter 6 for a $\lambda_2=600$ nm where no absorption occurs. The tests were performed as already described with various concentrations of FITC-labelled of IgG and also using, in another set of measurements, active fiber sections of only 5 cm. The results are reported in Table VI.

TABLE VI

| Concentration of labelled IgG in test cuvette (μg/ml) | Slope of rate curve a (mV/min) for fiber lengths 5 and 10 cm | |
|---|---|---|
| | 5 | 10 |
| 0.827 | 10.2 | 22.6 |
| 0.568 | 6.8 | 14.3 |
| 0.350 | 4.1 | 8.9 |
| 0.178 | 2.1 | 4.3 |
| 0.090 | 0.98 | 2.1 |
| 0.045 | 0.43 | 0.94 |

EXAMPLE 8

It was seen in the previous Example that tagging with a fluorescein derivative could be used to modify the absorption spectrum of a protein and, consequently, increase the sensitivity of the test of the present invention with regard to the unlabelled species. Of course, this system can also be used to measure unknown concentration of labelled AB, the ratio of which over that of the labelled species will then be rate determinant according to the scheme shown on FIG. 6. In the experiments, the results of which are reported in Table VII, the fixed concentration of labelled IgG was 1 μg/ml. The values reported in the first column are that of unlabelled IgG.

TABLE VII

| Unlabelled IgG concentration (μg/ml) | Slope of rate curves (arbitrary units) |
|---|---|
| 0 (i.e. 1 μg/ml of labelled IgG) | 24.3 |
| 0.09 | 19.7 |
| 0.83 | 10.2 |
| 4.14 | 2.4 |
| 9.2 | 0.84 |

EXAMPLE 9

The apparatus of FIG. 9 was operated under fluorescence measurement conditions, i.e. the filter 5 for the excitation light was for $\lambda_1=492$ nm and the value for filter 6 and for the additional excitation light blocking filter after the fiber back-end was for $\lambda_2=518$ nm.

The experiment was actually performed exactly as in Example 8 but measuring an increase of signal (emitted fluorescence) instead of a decrease as in absorption phenomena. As in Example 8, the analyte contained 1 μg/ml of fluorescent IgG+various concentrations of unlabelled human IgG as shown in the left column in the table.

TABLE VIII

| Unlabelled IgG concentration (μg/ml) | Slope of rate curves (arbitrary units) |
|---|---|
| 0 | 17.9 |
| 0.09 | 13.0 |
| 0.83 | 5.3 |
| 4.14 | 1.4 |
| 9.20 | 0.42 |

It should be clear to the reader that the results disclosed in Examples 1 to 9 have been used as the standards for comparison purposes with similar samples of unknown concentrations. Comparisons and computations can be done, as usual, visually or by electronic processing in the microcomputers attachable to the disclosed apparatuses.

We claim:

1. A method of determining the presence *and concentration* of an analyte in solution, which comprises the steps of:

(a) applying a film of a reaction to a surface of an optical waveguide *core* having a refractive index $n_1$;

(b) [injecting a light signal of a wave length λ into said waveguide at one end thereof and measuring at another end of said waveguide a light signal modification resulting from an evanescent light component associated with said signal in said waveguide, said light signal being internally reflected at an angle θ of internal reflection] *contacting said film with a solution of an analyte in a liquid phase of refractive index* $n_2$ less than $n_1$, whereby said analyte reacts with said reaction to form an analyte/reactant reaction product layer at the surface of said waveguide core, (c) [contacting said film with a solution of an analyte in a liquid phase of refractive index $n_2$ less than $n_1$ whereby said analyte reacts with said reactance to form a layer of analyte-reactant product on said waveguide of a thickness less than λ; and] *injecting a light signal of waveguide λ into said waveguide core at an input thereof, whereby said light signal is internally reflected through said waveguide core at an angle θ of internal reflection and evanescent wave component of said light signal interacts with said analyte/reactant product at the surface of said waveguide core which interaction results in a modification of said light signal representing presence and concentration of said analyte,*

(d) controlling the depth of penetration dp of said evanescent [light] *wave* component [associated with said signal in said waveguide] *into said liquid phase* in accordance with the relation:

$$dp = \frac{\lambda}{2\pi\,(\sin^2\theta - (n_2/n_1)^2)^{\frac{1}{2}}}$$

so that said depth of penetration dp substantially matches or exceeds the thickness of said [analyte-reactant] *analyte/reactant* product layer [and the measurement in step (b) takes place while the reaction occurs without interference from spurious signals from the liquid phase surrounding said layer.], *and*

*(e) measuring at an output of the waveguide core said light signal modification while the reaction occurs without interference from spurious signals from the liquid phase surrounding said layer.*

2. The method defined in claim 1 wherein [the] *said evanescent component has an* electric field [E of said evanescent component] *having a value E* at depth of penetration dp corresponding to the thickness of said reactant product layer [is], *said value being* at least 0.1 of the value Eo of the electric field at zero depth.

3. The method defined in claim 1 in which said modification [refers to] *is* the absorption of the light signal, *said light signal being injected into one end of said waveguide core and said output being at another end of said waveguide core,* said modification leading to a decrease with time of the light signal measured at [an] *said* output of said waveguide core.

4. The method defined in claim 1 in which said modification is the generation of a fluorescent light signal, said fluorescent light signal increasing with time as measured at [an] *said* output of said waveguide *core.*

5. The method defined in claim 1 in said *said* modification is the scattering of said light wave signal, the extent of such scattering increasing with time and being measurable partly laterally of the scattering region and partly at [an] *said* output of the waveguide *core.*

6. The method defined in claim 1 in which a polarized light signal is used and in which said modification affects elliptical polarization parameters of said signal.

7. The method defined in claim 1 in which the waveguide *core* is selected from [the] *a* light transparent plate, rod or fiber with refractive index of at least 1.4.

8. The method defined in claim 1 in which the waveguide g *core* is a single mode or multi-mode optical fiber.

9. The method defined in claim 1 in which a multimode fiber is used as said waveguide *core,* and comprising using modes sufficiently shallow, with regard to *an axis of* the fiber [axis], to ensure total reflection and sufficiently steep to ensure a high linear density of light signal/coating interaction sites.

10. The method defined in claim 1 in which the waveguide *core* is a multi-mode fiber and in which the modes are selected with an initial reflecting angle close to the critical angle, whereby in the course of the reaction a slight change in the refractive index $N_2$ $n_2$ of [the] *a* rare medium that occurs due to the growing of the analyte-reactant product will result in at least partial refraction of the *signal* outside the waveguide *core.*

11. The method defined in claim 1 wherein the light signal modification in step (b) is monitored with time, and [the] rate data so obtained is correlated with corresponding standard reference rate data obtained in a similar manner from calibrating samples of said analyte.

12. The method defined in claim 11 wherein a reference quantity of the analyte is contacted with said film while adding beforehand or simultaneously therewith a reference amount of reactant for causing the latter to competitively react with the analyte in the solution and said reference quantity on the surface *of said waveguide core.*

13. The method defined in claim 11 in which there is added in the analyte solution a tracer quantity of pure analyte in labelled form, the presence of a label in the reactant analyte product layer on the waveguide surface causing the said modification to the light signal travelling through said waveguide core, the magnitude of said modification being in direct relation with the ratio of labelled analyte in the solution.

14. The method defined in claim 11 wherein said film of said reactant on said surface is in excess of that stoichiometrically needed for binding the analyte in the solution to be determined, contacting said [coated] surface *having said film thereon* with the analyte solution for totally binding said analyte to be determined, adding to the analyte solution a reference amount of analyte in pure labelled form to react with the still unused excess of reactant, the presence of said label in the reactant analyte product causing the said light signal modification occurring to the light signal, the magnitude of said modification being in direct proportion to the ratio of the labelled analyte to the analyte originally in the solution.

15. The method defined in claim 11 in which the analyte [prossesses] *possesses* more than one binding side for specifically binding more than one kind of reactant, comprising contacting said surface coated with a first reactant with said analyte solution, adding a reference quantity of a second reactant for having said second reactant to bind to a second binding site of said analyte, the said light signal modification being the result of the binding of said second reactant on the said second binding site of the analyte bonded by a first binding site on said first reactant on the surface.

16. The method defined in claim 11 [in which] *comprising interpreting* said rate data are interpreted in terms of the slope of the rate curves pertaining to the reaction under test and [can be extrapolated] *extrapolating the rate curves* to determine equilibrium conditions.

* * * * *